(12) United States Patent
Lambris et al.

(10) Patent No.: US 10,632,170 B2
(45) Date of Patent: *Apr. 28, 2020

(54) ADMINISTRATION OF COMPSTATIN TO AN INDIVIDUAL FOR THE TREATMENT OF A TUMOR

(75) Inventors: John D. Lambris, Bryn Mawr, PA (US); Maciej M. Markiewski, Collegeville, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 396 days.

This patent is subject to a terminal disclaimer.

(21) Appl. No.: 12/918,101

(22) PCT Filed: Feb. 19, 2009

(86) PCT No.: PCT/US2009/001039
§ 371 (c)(1),
(2), (4) Date: Nov. 8, 2010

(87) PCT Pub. No.: WO2009/105217
PCT Pub. Date: Aug. 27, 2009

(65) Prior Publication Data
US 2011/0044983 A1    Feb. 24, 2011

Related U.S. Application Data

(60) Provisional application No. 61/066,229, filed on Feb. 19, 2008.

(51) Int. Cl.
*A61P 35/00* (2006.01)
*A61K 38/10* (2006.01)

(52) U.S. Cl.
CPC .................... *A61K 38/10* (2013.01)

(58) Field of Classification Search
None
See application file for complete search history.

(56) References Cited

U.S. PATENT DOCUMENTS

| | | | |
|---|---|---|---|
| 6,180,370 B1 | 1/2001 | Queen et al. | |
| 6,319,897 B1 | 11/2001 | Lambris et al. | |
| 7,491,530 B2 | 2/2009 | Dessain et al. | |
| 7,579,432 B2 | 8/2009 | Taylor | |
| 7,993,834 B2* | 8/2011 | Mass ............................ | 435/6.11 |
| 8,071,096 B2 | 12/2011 | MacKay | |
| 2005/0222027 A1* | 10/2005 | Chiang et al. ................... | 514/12 |
| 2005/0271660 A1* | 12/2005 | Wang ......................... | 424/144.1 |
| 2005/0271663 A1* | 12/2005 | Ignatovich ....... | A61K 47/48676 424/145.1 |
| 2007/0269434 A1* | 11/2007 | Chelsky ............... | C12Q 1/6886 424/138.1 |

FOREIGN PATENT DOCUMENTS

| | | |
|---|---|---|
| WO | WO 97/33603 * | 9/1997 |
| WO | WO 199733603 | 9/1997 |
| WO | WO 1999013899 | 3/1999 |
| WO | WO 2004026328 | 4/2004 |
| WO | WO 2007044668 | 4/2007 |
| WO | WO 2007070983 | 6/2007 |
| WO | WO 2009105217 | 8/2009 |

OTHER PUBLICATIONS

Written Opinion of the International Search Authority of PCT/US09/01039 (Aug. 19, 2010).*
Katragadda et al., J. Med. Chem. 49: 4616-4622, 2006.*
Morkis et al., Biochemical Society Transactions 30, Part 6: 1026-1036, 2002.*
Balkwill, et al., "Inflammation and cancer: back to Virchow?", Lancet, vol. 357, pp. 539-545 (2001).
Bhardwaj, et al., Harnessing the immune system to treat cancer, J. Clin. Invest., 117:1130-1136 (2007).
Bird, et al., "Single chain antigen binding proteins", Science, vol. 242, pp. 423-426 (1988).
Blank, et al., "PD-L1 inhibits the effector phase of tumor rejection by TCR transgenic CD8+ T cells", Cancer Res., vol. 64, pp, 1140-1145 (2004).
Burton, et al., "Human antibodies from combinatorial libraries", Adv. Immunol., vol. 57, pp. 191-280 (1994).
Carroll, et al., The complement system in regulation of adaptive immunity, Nature Immunol. 5:981-986 (2004).
Circolo, et al., promoter region generates deficient mice with extrahepatic expression of C3 mRNA,, Immunopharmacology 42:135-149 (1999).
Coussens, et al., "Inflammation and cancer", Nature, vol. 420, pp. 860-867. (2002).
Daniel, et al., "The Reduced Bactericidal Function of Complement C5-Deficient Murine Macrophages Is Associated with Defects in the Synthesis and Delivery of Reactive Oxygen Radicals to Mycobacterial Phagosomes", J. Immunol., vol. 177, pp. 4688-4698 (2006).
Dong, et al., "Tumor-associated B7-H1 promotes T-cell apoptosis: A potential mechanism of immune evasion", Nature Med., vol. 8, pp. 793-800 (2002).
Donin, et al., "Complement resistance of human carcinoma cells depends on membrane regulatory proteins, protein kinases and sialic acid", Clin. Exp. Immunol., vol. 131, pp. 254-263 (2003).
Dunn, et al, "Cancer immunoediting: from immunosurveillance to tumor escape", Nature Immunol., vol. 3, pp. 991-998 (2002).
Finch, et al., "Low-Molecular-Weight Peptidic and Cyclic Antagonists of the Receptor for the Complement Factor C5a", J. Med. Chem., vol. 42, pp. 1965-1974 (1999).
Fishelson, et al., "Obstacles to cancer immunotherapy: expression of membrane complement regulatory proteins (mCRPs) in tumors", Mol. Immunol., vol. 40, pp. 109-123 (2003).

(Continued)

*Primary Examiner* — Phillip Gambel
(74) *Attorney, Agent, or Firm* — Potter Anderson and Corroon LLP

(57) ABSTRACT

Methods for treating, preventing or delaying onset of tumor formation and other forms of cancer are disclosed. The methods involve administration of a complement inhibitor to inhibit C5a receptor signaling in the tumor microenvironment.

12 Claims, 7 Drawing Sheets

Specification includes a Sequence Listing.

(56) References Cited

OTHER PUBLICATIONS

Gelderman, et al., "Complement function in mAb-mediated cancer immunotherapy", Trends Immunol., vol. 25, pp. 158-164 (2004).
Gu, et 'al., "Construction and Expression of Mouse-Human Chimeric Antibody SZ-51 Specific for Activated Platelet P-Selectin", Thrombosis and Hematocyst, vol. 77, pp. 755-759 (1997).
Guo, et al., "Neutrophil C5a receptor and the outcome in a rat model of sepsis", Faseb J., vol. 17. pp. 1889-1891 (2003).
Guo, et al., "Role of C5A In Inflammatory Responses", Ann. Rev. Immunol., vol. 23, pp. 821-852 (2005).
Holland, et al., "Synthetic small-molecule complement inhibitors", Curr. Opin. Invest. Drugs, vol. 5, pp. 1164-1173 (2004).
Holtz, et al., "Should Tumor VEGF Expression Influence Decisions on Combining Metronomic Chemotherapy with Antiangiogenic Therapy? Preclinical Modeling in Ovarian Cancer", J. Transl. Med., vol. 6, p. 2 (2008).
Hopken, "The C5a chemoattractant receptor mediates mucosal defence to infection", Nature, vol. 383, pp. 86-89 (1996).
Houston, et al., "protein engineering of antibody binding sites; recovery of specific activity . . . ", Proc. Natl. Acad, Sci. USA, vol. 85, pp. 5879-5883 (1988).
Huber-Lang, et al., "Generation of C5a in the absence of C3: a new complement activation pathway", Nature Med., vol. 12, pp. 682-687 (2006).
Joshwich, et al., "Ligand Specificity of the Anaphylatoxin C5L2 Receptor and Its Regulation on Myeloid and Epithelial Cell Lines", J. Biol. Chem., vol. 281, pp. 39088-39095 (2006).
Kusmartsev, et al., "Antigen-Specific Inhibition of CD8+ T Cell Response by Immature Myeloid Cells in Cancer Is Mediated by Reactive Oxygen Species", J. Immunol., vol. 172, pp. 989-999 (2004).
Kusmartsev, et al., "Tumor-Associated CD8+ T Cell Tolerance Induced by Bone Marrow-Derived Immature Myeloid Cells", J. Immunol., vol. 175, pp. 4583-4592 (2005).
Lin, et al., "A cytokine-mediated link between innate immunity, inflammation, and cancer", J. Clin Invest., vol. 117, pp. 1175-1183 (2007).
Lin, et al., "Treatment of Established Tumors with a Novel Vaccine That Enhances Major Histocompatibility Class II Presentation of Tumor Antigen", Cancer Res., vol. 56, pp. 21-26 (1996).
Macor, et al., "Complement as effector system in cancer immunotherapy", Immunol. Lett., vol. 111, pp. 6-13 (2007).
Markiewski, et al., "C3a and C3b Activation Products of the Third Component of Complement (C3) Are Critical for Normal Liver Recovery after Toxic Injury", J. Immunol., vol. 173, pp. 747-754 (2004).
Markiewski, et al., "The role of complement in inflammatory diseases from behind the scenes into the spotlight", Am. J. Pathol., vol. 171, pp. 715-727 (2007).
Marx, et al., "Cancer's bulwark against immune attack: MDS cells", Science, vol. 319, pp. 154-156 (2008).
Mastellos, et al., "Novel monoclonal antibodies against mouse C3 interfering with complement activation: description of fine specificity and applications to various immunoassays", Mol. Immunol., vol. 40, pp. 1213-1221 (2004).
Matsumoto, et al., "Abrogation of the alternative complement pathway by targeted deletion of murine factor B", Proc. Natl. Acad. Sci. USA, vol. 94, pp. 8720-8725 (1997).
Monk, et al., "function, structure and therapeutic potential of complement C5a receptors", Br. J. Pharmacol., vol. 152, pp. 429-448 (2007).
Morikis, et al., "Design, Structure, Function and Application of Compstatin" Bioactive Peptides in Drug Discovery and Design: Medical Aspects,'IOS Press, pp. 235-246 (1999).
Proctor, et al., "Transdermal pharmacology of small molecule cyclic C5a antagonists", Adv. Exp. Med. Biol., vol. 586, pp. 329-345 (2006).
Ricklin, et al., "Complement-targeted therapeutics", Nature Biotechnol., vol. 25, pp. 1265-1275 (2007).
Sahu, et al., "Structure, functions, and evolution of the third complement component and viral molecular mimicry", Immunol. Res., vol. 17, pp. 109-121 (1998).
Sahu, et al., "Structure and biology of complement protein C3, a connecting link between innate and acquired immunity", Immunol. Res., vol. 180, pp. 35-48 (2001).
Sica, et al., "Altered macrophage differentiation and immune dysfunction in tumor development", J. Clin. Invest., vol. 117, pp. 1155-1166 (2007).
Strey, et al., "The Proinflammatory Mediators C3a and C5a Are Essential for Liver Regeneration", J. Exp. Med., vol. 198, pp. 913-923 (2003).
Swann, et al., "Immune surveillance of tumors", J. Clin. Invest., vol. 117, pp. 1137-1146 (2007).
Tuszynski, et al., "Thrombospondin promotes platelet aggregation", Blood, vol. 72, pp. 109-115 (1988).
Wessels, et al., "Studies of group B *streptococcal* infection in mice deficient in complement C3 or C4 demonstrate an essential role for complement in both innate and acquired immunity", Proc. Natl. Acad, Sci. USA, vol. 92, pp. 11490-11494 (1995).
Wright, et al., "Recombinant antibodies", Crit. Rev. Immunol., vol. 12, pp. 125-168 (1992).
International Search Report for PCT/US2009/01039 dated Aug. 17, 2009.
Communication issued by the European Patent Office dated May 14, 2012 for Patent Application No. EP09712731 with Supplementary European Search Report dated May 2, 2012.
Kohl, et al., "The C5a receptor antagonist PMX-53", Curr. Opin. Mol. Ther. vol. 8, pp. 529-538 (2006).

* cited by examiner

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial sequence
<220> FEATURE:
<223> OTHER INFORMATION: synthetic sequence
<220> FEATURE:
<221> NAME/KEY: DISULFID
<222> LOCATION: (2)..(12)

<400> SEQUENCE: 1

Ile Cys Val Val Gln Asp Trp Gly His His Arg Cys Thr
1               5                   10

<210> SEQ ID NO 2
```

```
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val, Gly, a dipeptide
      Thr-Asn, a dipeptide Thr-Ala, a tripeptide Thr-Ala-Asn
<220> FEATURE:
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 2

Xaa Xaa Cys Val Xaa Gln Asp Trp Gly Xaa His Arg Cys Xaa Xaa Xaa
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: synthetic sequence
<220> FEATURE:
<221> NAME/KEY: VARIANT
<222> LOCATION: (1)..(1)
<223> OTHER INFORMATION: Xaa is Gly or is missing
<220> FEATURE:
<221> NAME/KEY: VARIANT
<222> LOCATION: (2)..(2)
<223> OTHER INFORMATION: Xaa is Ile, Val, Leu, Ac-Ile, Ac-Val or Ac-Leu
<220> FEATURE:
<221> NAME/KEY: DISULFID
<222> LOCATION: (3)..(13)
<220> FEATURE:
<221> NAME/KEY: VARIANT
<222> LOCATION: (5)..(5)
<223> OTHER INFORMATION: Xaa is Trp or an analog of Trp
<220> FEATURE:
<221> NAME/KEY: VARIANT
<222> LOCATION: (8)..(8)
<223> OTHER INFORMATION: Xaa is Trp or an analog of Trp
<220> FEATURE:
<221> NAME/KEY: VARIANT
<222> LOCATION: (10)..(10)
<223> OTHER INFORMATION: Xaa is His, Ala, Phe or Trp
<220> FEATURE:
<221> NAME/KEY: VARIANT
<222> LOCATION: (14)..(14)
<223> OTHER INFORMATION: Xaa is L-Thr, D-Thr, Ile, Val, Gly, a dipeptide
      Thr-Asn, a dipeptide Thr-Ala, a tripeptide Thr-Ala-Asn
<220> FEATURE:
```

```
<221> NAME/KEY: VARIANT
<222> LOCATION: (15)..(15)
<223> OTHER INFORMATION: Xaa is Asn or Ala, or is missing
<220> FEATURE:
<221> NAME/KEY: VARIANT
<222> LOCATION: (16)..(16)
<223> OTHER INFORMATION: Xaa is Asn, or is missing

<400> SEQUENCE: 3

Xaa Xaa Cys Val Xaa Gln Asp Xaa Gly Xaa His Arg Cys Xaa Xaa Xaa
1               5                   10                  15
```

ADMINISTRATION OF COMPSTATIN TO AN INDIVIDUAL FOR THE TREATMENT OF A TUMOR

This is a U.S. national filing, pursuant to 35 U.S.C. § 371, of International Application No. PCT/US2009/001039, filed Feb. 19, 2009, which claims benefit of U.S. Provisional Application No. 61/066,229, filed Feb. 19, 2008, the entire contents of each of which are incorporated by reference herein.

This invention was made with government support under grant number CA112162 awarded by the National Institutes of Health. The government has certain rights in the invention Pursuant to 35 U.S.C. § 202(c), it is acknowledged that the United States government may have

FIELD OF THE INVENTION

This invention relates to the field of oncology and cancer therapy. Methods for treating, preventing or delaying onset of formation of malignant tumors during cancerous disease development are provided. The methods involve administration of a complement inhibitor to inhibit C5a receptor signaling in the treatment of a cancer.

BACKGROUND OF THE INVENTION

Various publications, including patents, published applications, technical articles and scholarly articles are cited throughout the specification. Each of these cited publications is incorporated by reference herein, in its entirety. Full citations for publications not cited fully within the specification are set forth at the end of the specification.

The diverse roles played by the immune system in cancer initiation and development are illustrated by two concepts: the "cancer immunoediting" theory, which postulates that the immune system protects the host against cancer development (Dunn et al., 2002, Nature Immunol. 3:991-998; Swann et al., 2007, J. Clin. Invest. 117:1137-1146) and the traditional concept that long-lasting inflammatory reactions facilitate malignant transformation and cancer progression (Coussens et al., 2002, Nature 420:860; Balkwill et al., 2001, Lancet 357:539-545; Bhardwaj et al., 2007, J. Clin. Invest. 117:1130-1136; Lin et al., 2007, J. Clin. Invest. 117:1175-1183; Blank et al., 2004, Cancer Res. 64:1140). Although an immune reaction develops against malignant tumor cells, tumors have the capacity to suppress this immune response, escaping from immune effector mechanisms (Swann et al., 2007, J. Clin. Invest. 117:1137; Blank et al., 2004, Cancer Res. 64:1140-1145; Dong et al., 2002, Nature Med. 8:793-800). Antigen-specific $CD8^+$ T cell tolerance, induced by myeloid-derived suppressor cells (MDSCs) recruited by tumors, is an example of one such suppression mechanism (Sica et al., 2007, J. Clin. Invest. 117:1155-1166; Kusmartsev et al., 2005, J. Immunol. 175: 4583-4592). Although mechanisms responsible for the suppressive phenotype of MDSCs vary, several studies postulate that MDSCs produce large quantities of reactive oxygen or nitrogen species (ROS or RNS, respectively), which directly inhibit the antigen-specific $CD8^+$ T cell-dependent immune response (Kusmartsev et al., 2004, J. Immunol. 172:989-999). In addition, L-arginine metabolism regulated by arginase-1 contributes to the generation of these reactive species and seems to have a central role for the suppression of T cells by MDSCs (Marx et al., 2008, Science 319:154-156). The immunosuppressive capacity of MDSCs is thought to be one of the major obstacles limiting the use of anti-cancer vaccines (Bhardwaj, 2007, J. Clin. Invest. 117: 1130-1136).

Another potential player in the response to cancer is the complement system, which has an essential role in inflammation and the innate immune response against infections (Markiewski et al., 2007, Am. J. Pathol. 171:715-727). Complement's wide-ranging activities link the innate immune response to the subsequent activation of adaptive immunity (Carroll, 2004, Nature Immunol. 5:981-986). Circulating complement proteins are activated by limited proteolysis occurring on the surface of pathogens or modified host cells. Some of the resulting cleavage products are deposited on pathogen or host cell surfaces, and others are released into body fluids, where they interact with specific receptors on various target cells. Of these complement components, the C3 protein is considered to be central to the complement cascade. Enzymatic cleavage of C3 leads to the production of the anaphylatoxin C3a, an inflammatory mediator and chemoattractant, and C3b (Sahu et al., 1998, Immunol. Res. 17:109-121). C3b plays a role in the opsonization and subsequent clearance of pathogens, but is also a main component of the C5 convertase, an enzyme complex that cleaves C5 to produce the anaphylatoxin C5a and C5b. The ensuing cell-surface deposition of the C5b fragment contributes to the formation of the pore-like membrane attack complex (MAC) within cellular membranes, whereas C5a is released and acts as an even more potent chemoattractant and inflammatory mediator than C3a (Markiewski et al., 2007, Am. J. Pathol. 171:715-727; Guo et al., 2005, Ann. Rev. Immunol. 23:821-852).

Formation of the MAC leads to the lysis of bacteria or other foreign cells and, under certain pathophysiological conditions, lysis of host cells, as well (Markiewski et al., 2007, Am. J. Pathol. 171:715-727). Given that several complement components have been found to be deposited in the tumor tissue of patients, the MAC was originally thought to contribute to the immunosurveillance of malignant tumors by complement (Fishelson et al., 2003, Mol. Immunol. 40:109-123; Donin et al., 2003, Clin. Exp. Immunol. 131: 254-263). Further studies revealed, however, that malignant tumor cells are protected against such complement-mediated lysis because they overexpress complement regulators that limit complement activation and deposition in situ, and, therefore, the formation of the MAC (Fishelson et al., 2003, Mol. Immunol. 40:109-123; Donin et al., 2003, Clin. Exp. Immunol. 131:254-263). It has recently been postulated that the ability of the MAC to lyse foreign and host cells might enhance the efficacy of cancer immunotherapies involving monoclonal antibodies specific for particular tumor antigens, since complement proteins enhance antibody-dependent cytotoxicity (Macor et al., 2007, Immunol. Lett. 111: 6-13; Gelderman et al., 2004, Trends Immunol. 25:158-164).

Despite investigation into the anti-cancer potential of the complement system, a distinctly different role for complement effectors as factors that might promote tumor growth has not yet been explored.

SUMMARY OF THE INVENTION

One aspect of the invention features a method for treating an individual having a malignant tumor, the method comprising administering a therapeutically effective amount of a complement inhibitor to the individual, wherein the complement inhibitor reduces or prevents C5a receptor signaling in the tumor, thereby preventing, reducing or delaying growth of the tumor. The methods of the invention may be applied to any individual, including humans and animals. In one embodiment, the individual is human.

The complement inhibitor can be one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof.

In certain embodiments, the complement inhibitor is a C5a inhibitor or a C5aR inhibitor. Selected C5a or C5aR inhibitors include, but are not limited to, acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof.

In other embodiments, the complement inhibitor is a C3 inhibitor. Selected C3 inhibitors include, but are not limited to, compstatin, a compstatin analog, a compstatin peptidomimetic, a compstatin derivative, or any combinations thereof.

In other embodiments, the complement inhibitor is a C4 inhibitor. Selected C4 inhibitors include, but are not limited to, anti-C4 antibodies.

In one embodiment, the complement inhibitor is administered at or targeted to the site of the tumor. Alternatively, the complement inhibitor can be administered systemically. The complement inhibitor may be administered alone, or together with, concurrently with, or sequentially before or after, one or more other anti-cancer treatments. Such treatments may include administration of other anti-cancer agents, or surgery, or radiation therapy, to name a few.

Another aspect of the invention features a pharmaceutical composition for treating tumors, the pharmaceutical composition comprising one or more complement inhibitors and at least one anti-cancer agent in a pharmaceutically acceptable medium.

The complement inhibitor can be one or more of a C5a inhibitor, a C5aR inhibitor, a C3 inhibitor, a C3aR inhibitor, a factor D inhibitor, a factor B inhibitor, a C4 inhibitor, a C1q inhibitor, or any combination thereof.

In certain embodiments, the complement inhibitor is a C5a inhibitor or a C5aR inhibitor. Selected C5a or C5aR inhibitors include, but are not limited to, acetyl-Phe-[Orn-Pro-D-cyclohexylalanine-Trp-Arg] (PMX-53), PMX-53 analogs, neutrazumab, TNX-558, eculizumab, pexelizumab or ARC1905, or any combination thereof.

In other embodiments, the complement inhibitor is a C3 inhibitor. Selected C3 inhibitors include, but are not limited to, compstatin, a compstatin analog, a compstatin peptidomimetic, a compstatin derivative, or any combinations thereof.

In other embodiments, the complement inhibitor is a C4 inhibitor. Selected C4 inhibitors include, but are not limited to, anti-C4 antibodies.

In one embodiment, the composition comprising the complement inhibitor is administered at or targeted to the site of the tumor or formulated for systemic administration.

Other features and advantages of the invention will be understood by reference to the drawings, detailed description and examples that follow.

BRIEF DESCRIPTION OF THE DRAWINGS

FIG. 2A and FIG. 2B, depicts involvement of the classical pathway in the activation of complement during tumor growth. FIG. 2A Tumor volumes for C4-deficient mice (C4-KO) and littermate wild-type controls (C4-WT) measured after tumor cell injection. "24-25 excised" indicates measurements of excised tumors. Horizontal lines represent mean tumor volumes for each group. The graph is representative of two independent experiments, with $n_1 \geq 14$ and $n_2=12$ mice per cohort (P<0.0001, two-way ANOVA). FIG. 2B Tumor volumes, as described in (FIG. 2A), for factor B-deficient mice (Factor B-KO) and littermate wild-type controls (Factor B-WT) (n=10 mice per cohort, P=0.6126, two-way ANOVA).

FIG. 3A through FIG. 3D, depicts how lack of C5aR signaling reduces tumor growth with efficiency similar to that of Taxol treatment. FIG. 3A. Tumor volumes for wild-type mice treated with C5aR antagonist (C5aRa), Taxol, or PBS (Control). "34 excised" indicates measurements of excised tumors. Horizontal lines represent mean tumor volumes for each group. The graph is representative for two independent experiments with $n_1 \geq 9$ and $n_2=5$ mice per cohort (*, P<0.05, two-way ANOVA, Bonferroni post test). FIG. 3B. Tumor volumes, as described in FIG. 3A, for C5aR-deficient mice (C5aR-KO) and littermate wild-type controls (C5aR-WT) (n=20 mice per cohort P<0.0001, two-way ANOVA). FIG. 3C. Tumor volumes, as described above, for C5aR-WT mice treated with PBS or Taxol, and C5aR-KO mice treated with PBS (n≥6 mice per cohort, P=0.004, two-way ANOVA). FIG. 3D. The relative expression of C5aR in TC-1 cells, immature dendritic cells (DC), and peritoneal macrophages is shown. Data are presented as a ratio of C5aR mRNA to $10^4$ GAPDH mRNA molecules. C5aR was considered to be present if more than five copies of mRNA were detected for every $10^4$ copies of GAPDH mRNA.

FIG. 4A through FIG. 4E, depicts the anti-tumor T cell response is enhanced in mice lacking C5aR signaling. FIG. 4A. CD8$^+$ T cell infiltration of end-point tumor tissue in controls (left) and C5aR antagonist (C5aRa)-treated mice. Fluorescence indicates CD8 expression on infiltrating T cells. Scale bar, 30 μm. FIG. 4B. Number of CD8$^+$ T cells infiltrating tumors versus tumor volumes, based on immuofluorescence studies in FIG. 4A, expressed as cells counted per 200× field (n≥8 mice per cohort, P=0.0180, r=−0.5653, Pearson correlation). FIG. 4C. Hematoxylin and eosin-stained end-point spleen sections from littermate wild-type (C5aR-WT, left) or C5aR-deficient (C5aR-KO, right) tumor-bearing mice. Asterisks indicate areas of white pulp. FIG. 4D. BrdU-positive end-point splenocytes in C5aR-WT (left) or C5aR-KO (right) mice bearing tumors. For FIG. 4C and FIG. 4D, n≥9 mice per cohort; scale bar, 60 μm. FIG. 4E. Tumor volumes for C5aR-KO and C5aR-WT mice treated with either IgG or CD8 antibody (α-CD8). "23-24 excised" indicates measurements of excised tumors. Horizontal lines represent mean tumor volumes for each group (n≥9 mice per cohort). Statistically significant differences (two-way ANOVA) were observed between: C5aR-WT+IgG vs. C5aR-KO+IgG (P=0.0003) and C5aR-KO+IgG vs. C5aR-KO+α-CD8 (P=0.0006).

FIG. 5A through FIG. 5K, depicts the migration of myeloid-derived cells into tumors is C5aR dependent. FIG. 5A through FIG. 5E. Expression of C5aR (white areas) versus isotype controls (grey areas) on MDSCs of wild-type mice (n≥5) from blood (FIG. 5A), spleen (FIG. 5B) and tumors (FIG. 5C-E). The same cells as shown in (FIG. 5D) were permeabilized before staining (FIG. 5E). FIG. 5F CD11b$^+$ cell infiltration of tumors from control (left) or C5aR antagonist (C5aRa, right) treated mice. The white dashed line represents the tumor border. Scale bar, 30 μm. FIG. 5G Quantification of CD11b$^+$ cells infiltrating tumors in relation to tumor volumes, based on FIG. 5F (n≥6 mice per cohort, P=0.0003, r=0.7670, Pearson correlation). FIG. 5H Representative contour plot showing characteristics of CD45$^+$CD11b$^+$Gr-1$^+$ cells from tumors from littermate wild-type (C5aR-WT) mice. R1, PMN-MDSCs; R2, MO-MDSCs. FIG. 5I The percentages of total MDSCs from tumors from C5aR-WT and C5aR-KO mice (P=0.23, t-test). FIG. 5J Ratio of PMN-MDSCs to MO-MDSCs in the total tumor MDSC population in C5aR-WT and C5aR-KO mice (P=0.001, t-test). FIG. 5K The percentages of CD11b$^+$Gr-1$^+$ MDSCs from CD45$^+$ splenocytes from C5aR-WT and C5aR-KO mice. (P=0.0024, t-test). For (i)-(k), bars represent mean values+SEM and n=16 mice per cohort.

FIG. 6A through FIG. 6D, depicts C5a upregulates CD11b expression in PMN-MDSCs. FIG. 6A and FIG. 6B. Induction of CD11b expression on PMN-MDSCs, as determined by flow cytometry analysis, obtained from the spleens (FIG. 6A) or tumors (FIG. 6B) of wild-type (WT) or C5aR-deficient (C5aR-KO) mice, after treatment with PMA or 10 nM C5a. Graphs show fold increase or decrease in the expression of CD11b in stimulated cells vs. baseline (equal to 1) in unstimulated cells from the same mice (WT or C5aR-KO). FIG. 6C and FIG. 6D Same analysis as described in FIG. 6A and FIG. 6B, but for MO-MDSCs. For FIG. 6A through FIG. 6D, bars represent mean values+SEM (n≥5 mice per cohort). The significance of the induction of CD11b expression was determined using one sample t-test (*, P=0.0232; , P=0.0040; *, P=0.0003; ****, P<0.0001).

FIG. 7A through FIG. 7I, depicts, C5a enhances the suppressive capabilities of tumor associated-MDSCs by regulating ROS and RNS production. FIG. 7A. Inhibition of PHA-induced proliferation of CD3$^+$ splenocytes from non-tumor-bearing wild-type mice in the presence of Gr-1$^+$. MDSCs from tumors from wild-type (C5aR-WT) or C5aR-deficient (C5aR-KO) mice (n=3 per cohort). FIG. 7B Representative histogram illustrating ROS and RNS production in MDSCs from tumors from C5aR-WT (grey area) and C5aR-KO (white area) mice. FIG. 7C Quantification of ROS and RNS production by MDSCs from tumors from C5aR-WT and C5aR-KO mice (P=0.0210, Wilcoxon). FIG. 7D Quantification of ROS and RNS production by PMN-MDSCs and MO-MDSCs from tumors of C5aR-WT and C5aR-KO mice (*P=0.0342, ** P=0.0005, Wilcoxon). For FIG. 7C and FIG. 7D, bars represent mean values of median fluorescence+SEM, and n≥12 mice per cohort. FIG. 7E Arginase-1 expression in tumors from control and C5aR antagonist-treated (C5aRa) mice. FIG. 7F. Quantification of immunoblot shown in FIG. 7E (P=0.0844, t-test). FIG. 7G Correlation between arginase-1 expression from FIG. 7F and tumor volumes in control and C5aRa-treated mice (Control P=0.0256, r=0.8147 and C5aR P=0.0105, r=0.7947, Pearson correlation). FIG. 7H. Induction of ROS and RNS in PMN-MDSCs, from the spleens of wild-type (C5aR-WT) or C5aR-deficient (C5aR-KO) mice, after treatment with PMA or 10 nM C5a. Graph shows fold increase in ROS and RNS in stimulated cells vs. baseline in unstimulated cells from the same mice. FIG. 7I. Same analysis as described in FIG. 7H but for MO-MDSCs. For FIG. 7H and FIG. 7I, bars represent mean values+SEM and n≥5 mice per cohort; *, P=0.0382; , P=0.0270; *, P=0.0245; ****, P<0.0092, one sample t-test.

DETAILED DESCRIPTION OF ILLUSTRATIVE EMBODIMENTS

Figure 1:
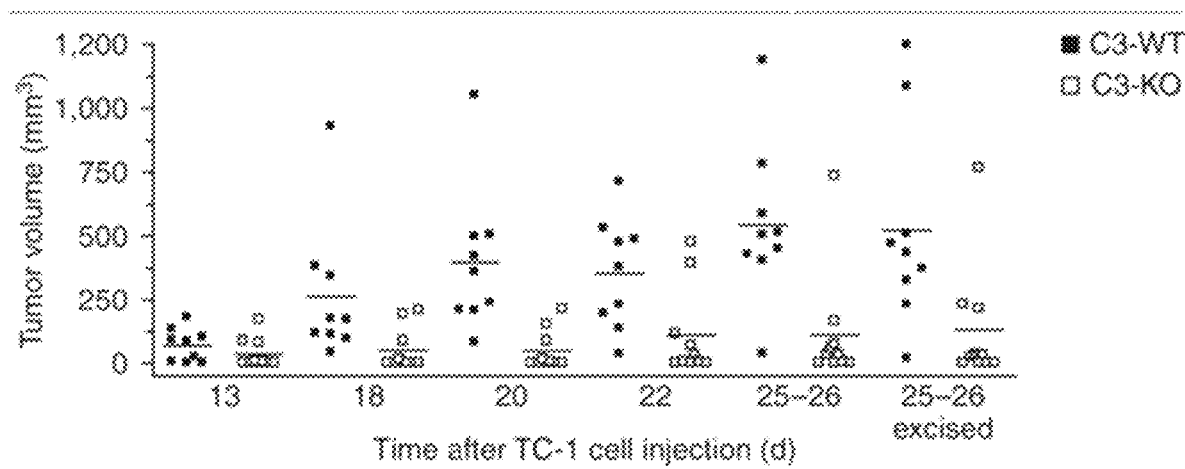
FIG. 1 depicts the role of complement activation in tumor growth. Tumor volumes for individual C3-deficient mice (C3-KO) and littermate wild-type controls (C3-WT) measured on various days after tumor cell injection. The last panel (25-26 excised) indicates volumes based on measurements obtained after mice were sacrificed and the tumors removed. Horizontal lines among each group of data points represent the mean tumor volume for that group. The graph is representative of three independent experiments, each with n=10 mice per cohort (P<0.0001 for the entire course of the experiment, two-way ANOVA).
Figure 2:
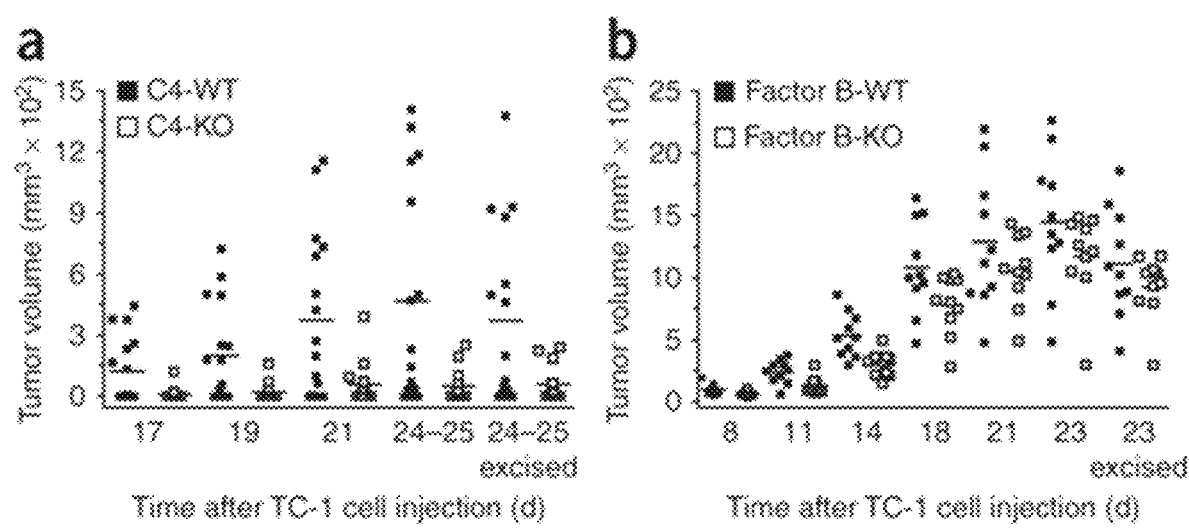
FIG. 2, comprising
Figure 3:
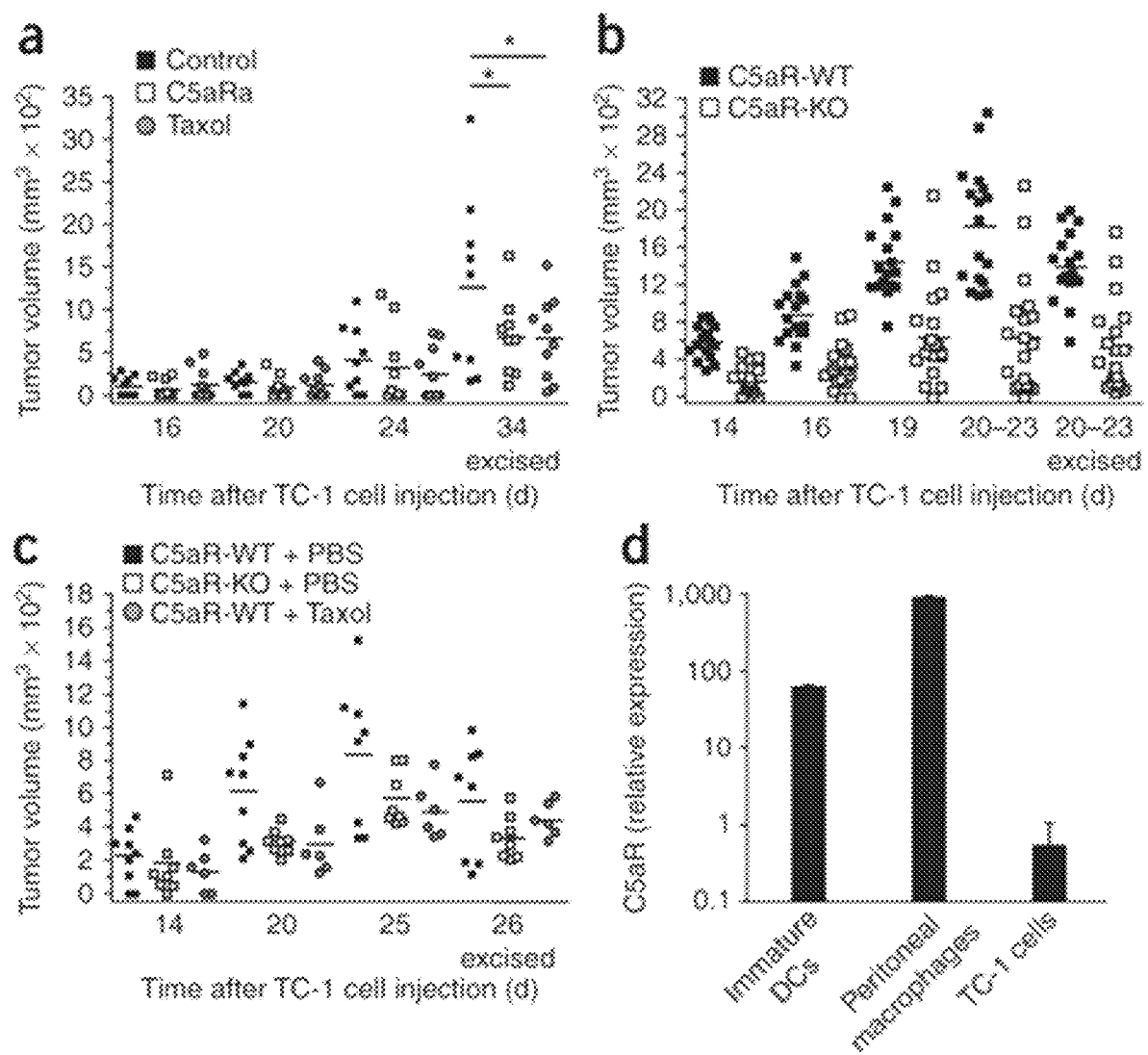
FIG. 3, comprising

Various terms relating to the methods and other aspects of the present invention are used throughout the specification and claims. Such terms are to be given their ordinary meaning in the art unless otherwise indicated. Other specifically defined terms are to be construed in a manner consistent with the definition provided herein.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used unless otherwise specified. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, a "complement inhibitor" is a molecule that prevents or reduces activation and/or propagation of the complement cascade that results in the formation of C5a or prevents binding of complement effectors to their receptors. A complement inhibitor can operate on one or more of the complement pathways, i.e., classical, alternative or lectin pathway.

As used herein, a "C3 inhibitor" is a molecule or substance that prevents or reduces the cleavage of C3 into C3a and C3b.

As used herein, a "C5a inhibitor" is a molecule or substance that prevents or reduces the activity of C5a.

As used herein, a "C5aR inhibitor" is a molecule or substance that prevents or reduces the binding of C5a to the C5a receptor.

As used herein, a "C3aR inhibitor" is a molecule or substance that prevents or reduces binding of C3a to the C3a receptor.

As used herein, a "factor D inhibitor" is a molecule or substance that prevents or reduces the activity of Factor D.

As used herein, a "factor B inhibitor" is a molecule or substance that prevents or reduces the activity of factor B.

As used herein, a "C4 inhibitor" is a molecule or substance that prevents or reduces the cleavage of C4 into C4b and C4a.

As used herein, a "C1q inhibitor" is a molecule or substance that prevents or reduces C1q binding to antibody-antigen complexes, virions, infected cells, or other molecules to which C1q binds to initiate complement activation.

Any of the inhibitors described herein may comprise antibodies or antibody fragments, as would be understood by the person of skill in the art.

"Treating" refers to any indicia of success in the treatment or amelioration of the disease or condition. Treating can include, for example, reducing or alleviating the severity of one or more symptoms of the disease or condition, or it can include reducing the frequency with which symptoms of a disease, defect, disorder, or adverse condition, and the like, are experienced by a patient.

"Preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented in that individual.

The term "treat or prevent" is sometimes used herein to refer to a method that results in some level of treatment or amelioration of the disease or condition, and contemplates a range of results directed to that end, including but not restricted to prevention of the condition entirely.

A "prophylactic" treatment is a treatment administered to a subject who does not exhibit signs of a disease or exhibits only early signs of the disease for the purpose of decreasing the risk of developing pathology associated with the disease. This term may be used interchangeably with the term "preventing," with the understanding that such prophylactic treatment or "prevention" does not establish a requirement for complete prevention of a disease in the entirety of the treated population.

As used herein, a "therapeutically effective amount" is the amount of a composition sufficient to provide a beneficial effect to the individual to whom the composition is administered.

It is understood that any and all whole or partial integers between any ranges set forth herein are included herein.

Description

The invention springs in part from the inventors' clear demonstration that complement deficiencies and pharmacological blockade of the C5a receptor reduces tumor growth. In one exemplary embodiment, the effect of C5a receptor antagonism was comparable to that achieved using the established anti-cancer drug paclitaxel. Inhibition of C5a receptor-mediated signaling amplified the anti-tumor CD8$^+$ T-cell response by decreasing the number of myeloid-derived suppressor cells within the tumor and their capacity to inhibit T-cell response to tumors.

The discoveries made in accordance with the present invention not only introduce a new complement-mediated mechanism of tumor-dependent immunosuppression but also provide support for the utility of a novel therapeutic option, complement inhibition, in anti-cancer therapy. This utility is particularly advantageous because of the relatively small number of side effects reported for complement-directed therapy (Kohl et al., 2006, Curr. Opin. Mol. Ther. 8:529-538; Ricklin et al., 2007, Nature Biotechnol. 25:1265-1275), as compared to the high toxicity associated with currently used anti-cancer chemotherapeutics.

The findings that support certain aspects of the invention, set forth in the Examples herein, indicate that the complement system and particularly C5a contribute to mechanisms that promote the growth of malignant tumors. The effects of treatment of wild-type mice with the C5aR inhibitor were comparable to those of the anti-cancer drug paclitaxel. Importantly, the dose of paclitaxel used was several times higher when compared to the therapeutic dose used for cancer patients (20 mg/kg/week vs. 3.3-4.3 mg/kg every 3 weeks for the treatment of ovarian carcinoma, according to the results of clinical studies provided by the manufacturer).

Generally, the activation of C5 requires prior activation of C3 (Sahu et al., 2001, Immunol. Rev. 180:35-48). However, under specific pathophysiological conditions, C5a can be generated in the absence of C3 (Huber-Lang et al., 2006, Nature Med. 12:682-687). Therefore, the similar degree of inhibition of tumor growth that was observed in C3-deficient, C5aR-deficient, and C5aR antagonist-treated mice indicates that C5 activation requires prior cleavage of C3. Furthermore, the presence of C3 cleavage products in tumor tissue indicates that C5a is generated locally in the tumor microenvironment and subsequently contributes to mechanisms supporting tumor growth. In view of these determinations, aspects of the present invention encompass inhibition of C5a receptor mediated signaling not only at the receptor, but at any point in the complement activation cascade leading to the production of C5a.

One aspect of the invention provides a method for alleviating and/or treating tumor formation and/or other forms of cancer in an individual. Specifically, the method comprises administering a complement inhibitor, as described in greater detail below.

In certain embodiments, complement inhibitors are used for the treatment or prevention of malignant solid tumors, as exemplified herein. Such tumors include, but are not limited to, ovarian and cervical tumors. Because of the apparent localized production of C5a in the tumor microenvironment, certain embodiments of the invention feature targeted delivery of the complement inhibitor to the site of the tumor; however, in the animal model described in the examples, the complement inhibitor was injected at a site away from the tumors. Targeted delivery to the tumor may be accomplished by physical targeting, e.g., by injection at the tumor site, or by chemical or biological targeting, e.g., by linking or associating the complement inhibitor with an agent that has an affinity for the tumor, such as an anti-tumor cell antibody. However, targeted delivery is not believed to be required or preferred in all cases.

Any inhibitor of C5a formation or activity may be used in the method of the invention. Inhibition of C5a formation or activity may be accomplished in a variety of ways. For instance, C5a activity may be inhibited directly by preventing or significantly reducing the binding of C5a to its receptor, C5aR. A number of C5aR inhibitors are known in the art. Acetyl-Phe-[Orn-Pro-D-cyclohexylalanine-Trp-Arg] (AcF[OPdChaWR]; PMX-53; Peptech) is a small cyclic hexapeptide that is a C5aR antagonist and is exemplified herein. Analogs of PMX-53 (e.g., PMX-201 and PMX-205) that also function as C5aR antagonists are also available (see for instance Proctor et al., 2006, Adv Exp Med Biol. 586: 329-45 and U.S. Pat. Pub. No. 20060217530). Neutrazumab (G2 Therapies) binds to C5aR, thereby inhibiting binding of C5a to C5aR. Neutrazumab (G2 Therapies) binds to extracellular loops of C5aR and thereby inhibits the binding of C5a to C5aR. TNX-558 (Tanox) is an antibody that neutralized C5a by binding to C5a.

C5a activity may also be inhibited by reducing or preventing the formation of C5a. Thus, inhibition of any step in the complement cascade which contributes to the downstream formation of C5a is expected to be effective in practicing the invention. Formation of C5a may be inhibited directly by inhibiting the cleavage of C5 by C5-convertase. Eculizumab (Alexion Pharmaceuticals, Cheshire, Conn.) is an anti-C5 antibody that binds to C5 and prevents its cleavage into C5a and C5b. Pexelizumab, an scFv fragment of Eculizumab, has the same activity. Similarly, ARC1905 (Archemix), an anti-05 aptamer, binds to and inhibits cleavage of C5, inhibiting the generation of C5b and C5a.

In another embodiment, formation of C5a is reduced or prevented through the use of a C3 inhibitor. Preferably, the C3 inhibitor is compstatin or a compstatin analog, derivative, aptamer or peptidomimetic. Compstatin is a small molecular weight disulfide bonded cyclic peptide having the sequence Ile-Cys-Val-Val-Gln-Asp-Trp-Gly-His-His-Arg-Cys-Thr (SEQ ID NO. 1). Examples of compstatin analogs, derivatives and peptidomimetics are described in the art. See, for instance, U.S. Pat. No. 6,319,897, WO/1999/013899, WO/2004/026328, and Morikis et al (1999, "Design, Structure, Function and Application of Compstatin" in Bioactive Peptides in Drug Discovery and Design: Medical Aspects, Matsoukas et al., eds., IOS Press, Amsterdam NL).

An exemplary compstatin analog comprises a peptide having a sequence: Xaa1-Cys-Val-Xaa2-Gln-Asp-Trp-Gly-Xaa3-His-Arg-Cys-Xaa4 (SEQ ID NO. 2);
wherein:
Xaa1 is Ile, Val, Leu, Ac-Ile, Ac-Val, Ac-Leu or a dipeptide comprising Gly-Ile;
Xaa2 is Trp or a peptidic or non-peptidic analog of Trp;
Xaa3 is His, Ala, Phe or Trp;
Xaa4 is L-Thr, D-Thr, Ile, Val, Gly, or a tripeptide comprising Thr-Ala-Asn, wherein a carboxy terminal —OH of any of the L-Thr, D-Thr, Ile, Val, Gly or Asn optionally is replaced by —NH$_2$; and the two Cys residues are joined by a disulfide bond. Xaa1 may be acetylated, for instance, Ac-Ile. Xaa2 may be a Trp analog comprising a substituted or unsubstituted aromatic ring component. Non-limiting examples include 2-napthylalanine, 1-naphthylalanine, 2-indanylglycine carboxylic acid, dihydrotryptophan or benzoylphenylalanine.

Another exemplary compstatin analog comprises a peptide having a sequence: Xaa1-Cys-Val-Xaa2-Gln-Asp-Xaa3-Gly-Xaa4-His-Arg-Cys-Xaa5 (SEQ ID NO. 3);
wherein:
Xaa1 is Ile, Val, Leu, Ac-Ile, Ac-Val, Ac-Leu or a dipeptide comprising Gly-Ile;
Xaa2 is Trp or an analog of Trp, wherein the analog of Trp has increased hydrophobic character as compared with Trp, with the proviso that, if Xaa3 is Trp, Xaa2 is the analog of Trp;
Xaa3 is Trp or an analog of Trp comprising a chemical modification to its indole ring wherein the chemical modification increases the hydrogen bond potential of the indole ring;
Xaa4 is His, Ala, Phe or Trp;
Xaa5 is L-Thr, D-Thr, Ile, Val, Gly, a dipeptide comprising Thr-Asn or Thr-Ala, or a tripeptide comprising Thr-Ala-Asn, wherein a carboxy terminal —OH of any of the L-Thr, D-Thr, Ile, Val, Gly or Asn optionally is replaced by —NH$_2$;

and the two Cys residues are joined by a disulfide bond. The analog of Trp of Xaa2 may be a halogenated trpytophan, such as 5-fluoro-1 1-tryptophan or 6-fluoro-1-tryptophan. The Trp analog at Xaa2 may comprise a lower alkoxy or lower alkyl substituent at the 5 position, e.g., 5-methoxytryptophan or 5-methyltryptophan. In other embodiments, the Trp analog at Xaa 2 comprises a lower alkyl or a lower alkenoyl substituent at the 1 position, with exemplary embodiments comprising 1-methyltryptophan or 1-formyltryptophan. In other embodiments, the analog of Trp of Xaa3 is a halogenated tryptophan such as 5-fluoro-1-tryptophan or 6-fluoro-1-tryptophan.

Other C3 inhibitors include vaccinia virus complement control protein (VCP) and antibodies that specifically bind C3 and prevent its cleavage.

In other embodiments, formation of C5a is reduced or prevented through the use of an inhibitor of complement activation prior C3 cleavage, e.g., in the classical or lectin pathways of complement activation. Non-limiting examples of such inhibitors include, but are not limited to: (1) factor D inhibitors such as diisopropyl fluorophosphates and TNX-234 (Tanox), (2) factor B inhibitors such as the anti-B antibody TA 106 (Taligen Therapeutics), (3) C4 inhibitors (e.g., anti-C4 antibodies) and (4) C1q inhibitors (e.g., anti-C1q antibodies). Likewise, inhibitors of signaling via the C3a receptor are also contemplated as being useful in the present invention.

Antibodies useful in the present invention, such as antibodies that specifically bind to either C4, C3 or C5 and prevent cleavage, or antibodies that specifically bind to factor D, factor B, C1q, or the C3a or C5a receptor, can be made by the skilled artisan using methods known in the art. See, for instance, Harlow, et al. (1988, In: Antibodies, A Laboratory Manual, Cold Spring Harbor, N.Y.), Tuszynski et al. (1988, Blood, 72:109-115), U.S. patent publication 2003/0224490, Queen et al. (U.S. Pat. No. 6,180,370), Wright et al., (1992, Critical Rev. in Immunol. 12(3,4):125-168), Gu et al. (1997, Thrombosis and Hematocyst 77(4):755-759) and Burton et al., (1994, Adv. Immunol. 57:191-280). Anti-C3 and anti-C5 antibodies are also commercially available.

The invention encompasses the use of pharmaceutical compositions comprising a complement inhibitor to practice the methods of the invention. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

The formulations of the pharmaceutical compositions described herein may be prepared by any method known or hereafter develop in the art of pharmacology. In general, such preparatory methods include the step of bringing the active ingredient into association with a carrier or one or more other accessory ingredients, and then, if necessary or desirable, shaping or packaging the product into a desired single- or multi-does unit.

As used herein, the term "pharmaceutically-acceptable carrier" means a chemical composition with which a complement inhibitor may be combined and which, following the combination, can be used to administer the complement inhibitor to a mammal.

As used herein, the term "physiologically acceptable" ester or salt means an ester or salt form of the active ingredient which is compatible with any other ingredients of the pharmaceutical composition, which is not deleterious to the subject to which the composition is to be administered.

The pharmaceutical compositions useful for practicing the invention may be administered to deliver a dose of between 1 ng/kg/day and 100 mg/kg/day. In one embodiment, the invention envisions administration of a dose which results in a concentration of a complement inhibitor between 1 µM and 10 µM in an individual diagnosed with or at risk of developing cancer. While the precise dosage administered will vary depending upon any number of factors, including but not limited to, the type of patient and type of disease state being treated, the age of the patient and the route of administration. Preferably, the dosage of the compound will vary from about 1 mg to about 10 g per kilogram of body weight of the patient. More preferably, the dosage will vary from about 10 mg to about 1 g per kilogram of body weight of the patient.

The pharmaceutical composition may be administered to a patient as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the patient, as described above.

A single complement inhibitor may be administered or two or more different complement inhibitors may be administered in the practice of the method of the invention. In one embodiment of the invention, the method comprises administration of only a complement inhibitor. In other embodiments, other biologically active agents are administered in addition to the complement inhibitor in the method of the invention. Non-limiting examples of other biologically active agents useful in the invention include various classes of chemotherapy drugs, including platinum complexes (such as carboplatin), mitotic inhibitors (such as paclitaxel), alkylating agents, antimetabolites, antitumor antibiotics and DNA topoisomerase inhibitors. The method may also be practiced with on-going treatment of the precipitating illness or condition, such as radiation therapy.

Pharmaceutical compositions that are useful in the methods of the invention may be administered systemically in oral solid formulations, parenteral, ophthalmic, suppository, aerosol, topical or other similar formulations. Such pharmaceutical compositions may contain pharmaceutically-acceptable carriers and other ingredients known to enhance and facilitate drug administration. Other formulations, such as nanoparticles, liposomes, resealed erythrocytes, and immunologically based systems may also be used to administer a complement inhibitor according to the methods of the invention.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, in microbubbles for ultrasound-released delivery or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents including replacement pulmonary surfactants; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, Remington's Pharmaceutical Sciences, Mack Publishing Co., Easton, Pa., which is incorporated herein by reference.

The following examples are provided to describe the invention in greater detail. They are intended to illustrate, not to limit, the invention.

Example 1

This example describes materials and procedures, the results of which are set forth in the subsequent examples.

In Vivo Studies and Reagents.

All mouse experiments were performed according to the National Institutes of Health (NIH) guidelines. Mice deficient in complement component C3, C4, factor B and the C5a receptor (C5aR)-deficient mice utilized in our studies have been previously described (Circolo, et al., 1999, Immunopharmacology 42, 135-149; Wessels, et al., 1995, Proc. Natl. Acad. Sci. USA 92, 11490-11494; Matsumoto, et al. 1997, Proc. Natl. Acad. Sci. USA 94, 8720-8725; Hopken, 1996, Nature 383, 86-89). Mice deficient in C4 and C57BL/6 mice were purchased from The Jackson Laboratory. Mice were backcrossed for at least nine generations onto a C57BL/6 background, and their homozygous wild-type littermates were used as controls. Mice were housed in an animal facility of the University of Pennsylvania, within a barrier, on a 12-h light/dark cycle. Water and standard rodent diet were provided ad libitum.

To establish TC-1 tumors, male and female mice 6-16 weeks of age were anesthetized and injected subcutaneously (s.c.) with $1 \times 10^5$ TC-1 cells in the right or left rear flank. The tumorigenic TC-1 cell line, described previously (Lin et al., 1996, Cancer Res. 56:21-26), was obtained from the American Type Culture Collection (ATCC Number CRL-2785). Beginning about 2 weeks after cell injection, mice were anesthetized, and their tumors were measured with calipers every 2-4 days until the tumor size required sacrificing of the animals. Measurements were taken in two dimensions (length and width) because the depth of the tumor was difficult to assess in live animals. The depth of the tumor was therefore estimated based on the smaller (width) measurement, and the volume of the tumor was calculated using the formula: (length×width×depth)÷2. One hour prior to sacrifice, 5-bromo-2'-deoxyuridine (BrdU; Sigma) was injected intraperitoneally (i.p.) into mice at a single dose of 50 mg/kg for further assessment of tumor or immune cell proliferation. At the time of sacrifice, clinical status was assessed, the mice were anesthetized, blood was harvested from the inferior vena cava (with 50 mM EDTA), and the spleens and tumors were removed. Excised tumors were measured in three dimensions to obtain an accurate volume and then weighed. Tumors and spleens were cut into sections for cell isolation, histologic examination, or freezing.

To achieve a pharmacological blockade of C5aR, C57BL/6J mice were injected s.c. with 1 mg/kg of the cyclic hexapeptide AcF[OPdChaWR] (C5aR antagonist), in ~400 µl of PBS, every 2-3 days beginning 1 week after tumor cell injection (3.3 µmol/kg/week). The C5aR antagonist was synthesized in our laboratory as previously described[25]. This antagonist has been shown to specifically block C5a-mediated effects in various rodent disease models (Kohl et al., 2006, Curr. Opin. Mol. Ther. 8:529-538; Holland et al., Curr. Opin. Invest. Drugs 5:1164-1173). Paclitaxel (Taxol; Mayne Pharma, Inc.) at a dose of 20 mg/kg in 400 µl PBS was injected i.p. into mice once per week (23 µmol/kg/week, $LD_{50}$=128 mg/kg according to the manufacturer) starting 1 week after tumor cell injection. Control mice in the experiments utilizing C5aR antagonist or Taxol were injected s.c., or i.p., respectively, with ~400 µl PBS alone, or in some cases, s.c. with the cyclic hexapeptide AcF[OPdChaA(d)R] (Finch et al., 1999, J. Med. Chem. 42:1965-1975; Johswich et al., 2006, J. Biol. Chem. 281:39088-39095). The pattern of the administration of this control peptide to mice followed that described for the C5aR antagonist.

To deplete $CD8^+$ T cells, mice were injected i.p. with rat anti-mouse CD8 monoclonal antibody (mAb 53-6.72) at a dose of 200 µg per mouse for 3 consecutive days. To maintain $CD8^+$ T cell depletion, injections were repeated every 2-3 days beginning from day 6. This regimen of administration resulted in approximately 95% depletion of $CD8^+$ T cells from peripheral blood and spleens of mice without tumors, as evaluated by flow cytometry analysis (data not shown). The rat anti-mouse CD8 antibody was purified from ascites produced in nude BALB/c mice (Cocalico Biologicals, Inc.) inoculated with Hybridoma cell line clone 53-6.72 (ATCC), using a standard protocol of ammonium sulfate and caprylic acid precipitations. To ensure endotoxin-free antibody solution, Detoxi-Gel™ Affinity Pack™ kit (Thermo Scientific, Pierce) was used for LPS removal.

All compounds used for in vivo studies were tested to be LPS free.

Tissue Processing, Cell Isolation and Purification.

Portions of tumors and spleens were fixed in 10% formalin, frozen in OCT medium at −70° C. or used for cell isolation. Fixed samples were routinely processed for histological evaluation and immunohistochemical staining. Frozen samples were cut with a cryostat into 5-µm thick sections for immunofluorescent staining. Blood samples, after erythrocyte lysis, were analyzed by flow cytometry to assess the expression of surface markers and C5aR by white blood cells. Portions of tumors and spleens were mechanically disaggregated in order to obtain single-cell suspensions. Erythrocytes were removed prior to cell culture or staining by treatment of cell suspensions with 155 mM $NH_4Cl$, 10 mM $KHCO_3$, and 1 mM EDTA, pH 7.3, for 5 min on ice. Myeloid precursors were selected by means of magnetic sorting. In brief, single-cell suspensions obtained from the tumors were pre-incubated with anti-mouse CD16/CD32 mAb (2.4G2) from BD Biosciences to block Fcγ receptors. The cells were then incubated with biotinylated anti-mouse Gr-1 (RB6-8C5) from BD Biosciences for 30 min, washed, and incubated with BD IMag Streptavidin Particles Plus (BD Biosciences) for 30 min at 4° C. and separated using an IMagnet (BD Biosciences).

Cell Proliferation, Apoptosis and Angiogenesis.

The morphology of tumors and spleens was assessed by light microscopy (Olympus BX 60) of hematoxylin and eosin-stained 5-µm paraffin sections. To assess the number of cells in the S phase of the cell cycle, paraffin sections from tumors and spleens were stained with anti-BrdU. The presence of apoptotic cells in tumor sections was determined by staining for the activated caspase-3 site on cytokeratin 18. Both assays were performed as described previously (Markiewski et al., 2004, J. Immunol. 173:747-754). The microvascular density of engrafted tumors was evaluated by immunofluorescent staining for CD31 expression on endothelial cells in frozen sections. The bound biotinylated anti-CD31 (MEC 13.3-BD Biosciences) was visualized with a streptavidin-rhodamine complex (BD Biosciences). Fluorescence was evaluated by standard fluorescent microscopy (Olympus BX 60 microscope). BrdU incorporation into tumor cells and the microvascular density of tumors were quantified in 5-10 microscopic fields (400× for BrdU and 100× for microvascular density) with the use of ImageJ image analysis software (NIH, Bethesda, Md.), and mean values were calculated. Apoptosis was assessed in a semi-quantitative manner: Scores from 0 to 4 were assigned to sections, depending on the size of the area occupied by apoptotic cells. All analyses were performed in a blinded fashion.

Complement Deposition and Immune Cell Infiltration.

The deposition of C3 cleavage products in tumor tissue was detected using a rat anti-mouse C3 mAb (clone 2/11), as described previously (Mastellos et al, 2004, Mol. Immunol. 40:1213-1221). This mAb specifically recognizes epitopes of C3 cleavage products (C3b, iC3b and C3c), but not inactive C3. Therefore, the positive reactivity in the tissue is thought to be associated with the activation of the complement cascade and C3 cleavage. C1q and MBL deposition were evaluated with the use of a rat anti-mouse C1q mAb (Abcam, Inc.) and a polyclonal goat anti-mouse MBL (Santa Cruz Biotechnology, Inc.), respectively. These sections were co-stained with the use of biotinylated anti-mouse CD31 to visualize tumor vasculature. CD8+ T cell and myeloid-origin cell infiltrations of tumors were analyzed using anti-mouse CD8 and anti-mouse CD11b, respectively. Isotypic rat IgGs were used as a negative control. Anti-CD31, anti-CD8 and anti-CD11b and isotype controls were purchased from BD Biosciences. Primary antibodies bound in tissue were detected with donkey anti-rat or anti-goat Cy2-conjugated antibodies (The Jackson Laboratory), except for anti-CD31, which was visualized with a streptavidin-rhodamine complex (BD Biosciences). Immunofluorescent staining was performed on frozen, 5-μm-thick sections. For detection of complement deposition, green and red fluorescence images were merged with the use of Spot software (Diagnostic instruments, Inc.). CD8+ tumor infiltrates were quantified using ImageJ image analysis software (NIH), positive cells were counted in whole tissue sections and means were calculated. The magnitude of CD11b+ infiltrates was assessed in a semi-quantitative manner because of the relatively low numbers of infiltrating cells. Scores from 0 to 5 were assigned to sections, according to the relative intensity of the infiltrates. In addition, the distribution of infiltrating cells was analyzed. All analyses were performed in a blinded fashion.

Fluorescence-Activated Cell-Sorting Analyses.

Single-cell suspensions were pre-incubated with anti-mouse CD16/CD32 mAb (Fc block, 2.4G2; BD Pharmingen) to block Fcγ receptors, then incubated with primary antibody. Fluorochrome-conjugated mAbs against mouse CD3 (17A2), CD4 (L3T4), CD8 (53-6.7), CD11b (M1/70), CD25 (PC61), CD45 (30-F11), CD69 (H1.2F3) and Gr-1 (RB6-8C5), (all from BD Biosciences) were used according to the manufacturer's instructions. In order to determine C5aR cell-surface expression, cells were sequentially incubated with rabbit polyclonal anti-mouse C5aR (C1150-32, BD Biosciences) or rabbit isotype (BD Pharmingen, 550875) and FITC-conjugated anti-rabbit IgG (F0112, R&D Systems), or with rat anti-mouse C5aR (mAb clone 20/70 Hycult biotechnology b.v., distributor-Cell science Inc.) or rat isotype (BD Pharmingen, 553928) followed by FITC-conjugated anti-rat IgG (Zymed-Invitrogen). For some experiments cells were permeabilized with the use of fixation and perm/wash buffers (BD Biosciences) prior to C5aR staining. Stained cells were subjected to six-color flow cytometry on a FACSCanto flow cytometer (BD Biosciences) using FlowJo software (Tree Star Inc.).

Preparation of CFSE-Labeled T Cells.

In order to obtain cells for proliferation studies, spleens were harvested from naive C57BL/6J mice and mechanically disrupted by passage through 100-μM mesh cups to obtain single-cell suspensions. After lysis of red blood cells, the splenocytes were pooled, pelleted by centrifugation, and washed twice in serum-free RPMI. Splenocytes were then labeled with 5,6-carboxyfluorescein diacetate succinimidyl ester (CFSE) (Molecular Probes), as follows: Cells were washed with ice-cold PBS, resuspended at $5 \times 10^6$ cells/ml in ice-cold PBS, and labeled by diluting the 0.5 mM CFSE stock 1,000-fold into the cell suspension (final concentration, 0.5 μM) and incubating the cells for 10 min at 37° C. After labeling, fetal calf serum was added to 5% final concentration, and the cells were immediately centrifuged and washed with ice-cold PBS.

Assay for Suppression of T Cell Proliferation.

The suppressive effect of MDSCs on T cell proliferation was assessed in co-culture assays: CFSE-labeled splenocytes ($1 \times 10^5$) were co-cultured with MDSCs ($1 \times 10^5$) in the presence of 5 μg/ml PHA (Sigma) for 5 days in RPMI 10% FBS at 37° C. in a 5% $CO_2$ atmosphere. T cell proliferation was determined by flow cytometry. For this purpose, non-adherent cells were recovered from the co-cultures and stained with fluorochrome-labeled anti-mouse CD3 (BD Bioscience) after blocking Fc receptors. Dilution of the CFSE signal in the FITC channel among CD3 gated cells was considered indicative of proliferation. CFSE-labeled splenocytes cultured with PHA in the absence of MDSCs (maximum proliferation, lowest CFSE signal) and equally labeled non-stimulated splenocytes (basal proliferation, highest CFSE signal) were used as controls.

Quantitative Real-Time PCR Analysis.

Expression of C5aR was analyzed at the mRNA level by quantitative real-time reverse transcription (RT)-PCR analysis. Total RNA was isolated with TRIzol reagent (Invitrogen), and the High Capacity cDNA Reverse Transcription Kit (Applied Biosystems) was used for reverse transcription of RNA into DNA according to the manufacturer's instructions. The SYBR® Green PCR Master Mix kit (Applied Biosystems) was used for real-time PCR. The absolute quantification method was used by generating standard curves for genes of interest and reference. Each amplification experiment was performed in 96-well optical-grade PCR plates covered with optical tape in the AbiPrism 7700 Sequence Detection System (Applied Biosystems) using suitable forward and reverse primers. The cDNA load was normalized to mouse glyceraldehyde-3-phosphate dehydrogenase (GAPDH) using suitable forward and reverse primers. Data were expressed as relative units, normalized to those for $10^4$ GAPDH mRNA molecules. Molecules were considered to be present if more than five copies of mRNA were detected for every $10^4$ copies of GAPDH mRNA.

Preparation of Dendritic Cells and Macrophages.

Bone marrow cells were dispersed by vigorous pipetting and cultured in RPMI-1640 supplemented with penicillin (100 μg/ml), streptomycin (100 U/ml), L-glutamine (2 mM), 2-mercaptoethanol (50 μM; Sigma), and 10% heat-inactivated FBS in the presence of 20 ng/ml of recombinant mouse granulocyte-macrophage colony-stimulating factor (GM-CSF, 315-03, Peprotech Inc.) for 8 days. GM-CSF was replenished on days 3 and 6. In some experiments, maturation was induced by culturing the cells for 2 days in the presence of 10 ng/ml GM-CSF, 20 ng/ml mouse tumor necrosis factor (TNF, 315-01A, Peprotech), and 1 μg/ml bacterial lipopolysaccharide (LPS from *E. coli*, serotype 0111:B4, L2630, Sigma). Mouse peritoneal cells were obtained by washing the peritoneal cavity of C57BL/6J mice with complete medium.

ROS and RNS Production.

The oxidation sensitive dye 2'-7'-dichloro dihydrofluorescein diacetate ($H_2DCFDA$) (Molecular Probes) was used for the measurement of ROS and RNS production in cells isolated from tumors or spleens. The excised tumors and spleens were mechanically disintegrated to obtain a single-cell suspension. Cells resuspended in DMEM were incubated with 2 µM of dye at 37° C. for 15 min. After washing with PBS, cells were stained for flow cytometry analysis as described above. MDSCs were distinguished from other cells present in the cell suspension as a viable $CD45^+$ $CD11b^+Gr-1^+$ cell population, and the fluorescence intensity was estimated in the channel suitable for FITC according to the manufacturer's instruction. The amounts of ROS and RNS in cells were proportional to the intensity of fluorescence and were expressed as median fluorescence for gated populations. For some experiments, in addition to incubation with $H_2DCFDA$, freshly isolated cells were simultaneously stimulated by 1, 10, or 100 nM of recombinant mouse C5a expressed as previously described (Strey et al., 2003, J. Exp. Med. 198:913-923) or 1 µM of phorbol myristate acetate (PMA; Sigma-Aldrich). Preliminary experiments have shown that stimulation of cells with 10 nM C5a induced the highest induction of ROS and RNS production.

Immunoblots.

Whole-cell extracts were prepared from tumor tissue mechanically disrupted in lysis buffer (20 mM HEPES, pH 7.4, 0.2 mM EDTA, 420 mM NaCl, 1.5 mM $MgCl_2$, 20% glycerol) treated with protease and phosphatase inhibitors (1 mM DTT, 0.1 mM PMSF, 0.1 mM $Na_3VO_4$, 1 mM NaF, 1 mM β-glycerophosphate, and 2 µg/ml each of antipain dihydrochloride, aprotinin, bestatin and leupeptin). For each protein sample, 40 µg was electrophoresed on a 12% polyacrylamide gel and transferred to a PVDF membrane. Membranes were incubated overnight at 4° C. with mouse monoclonal arginase I (8C9) antibody (Santa Cruz Biotechnology) or mouse monoclonal β-actin (AC-15) antibody (Abcam). Primary antibody binding was detected using HRP-conjugated anti-mouse antibody (Bio-Rad Laboratories, Inc.) and chemiluminescence (Amersham Pharmacia Biotech, Inc.). Protein loading was normalized according to the abundance of β-actin, with Ponceau S-stained membranes used for verification. Protein expression was quantified by densitometry using ImageQuant software (Molecular Dynamics).

Statistics.

Figure 4:
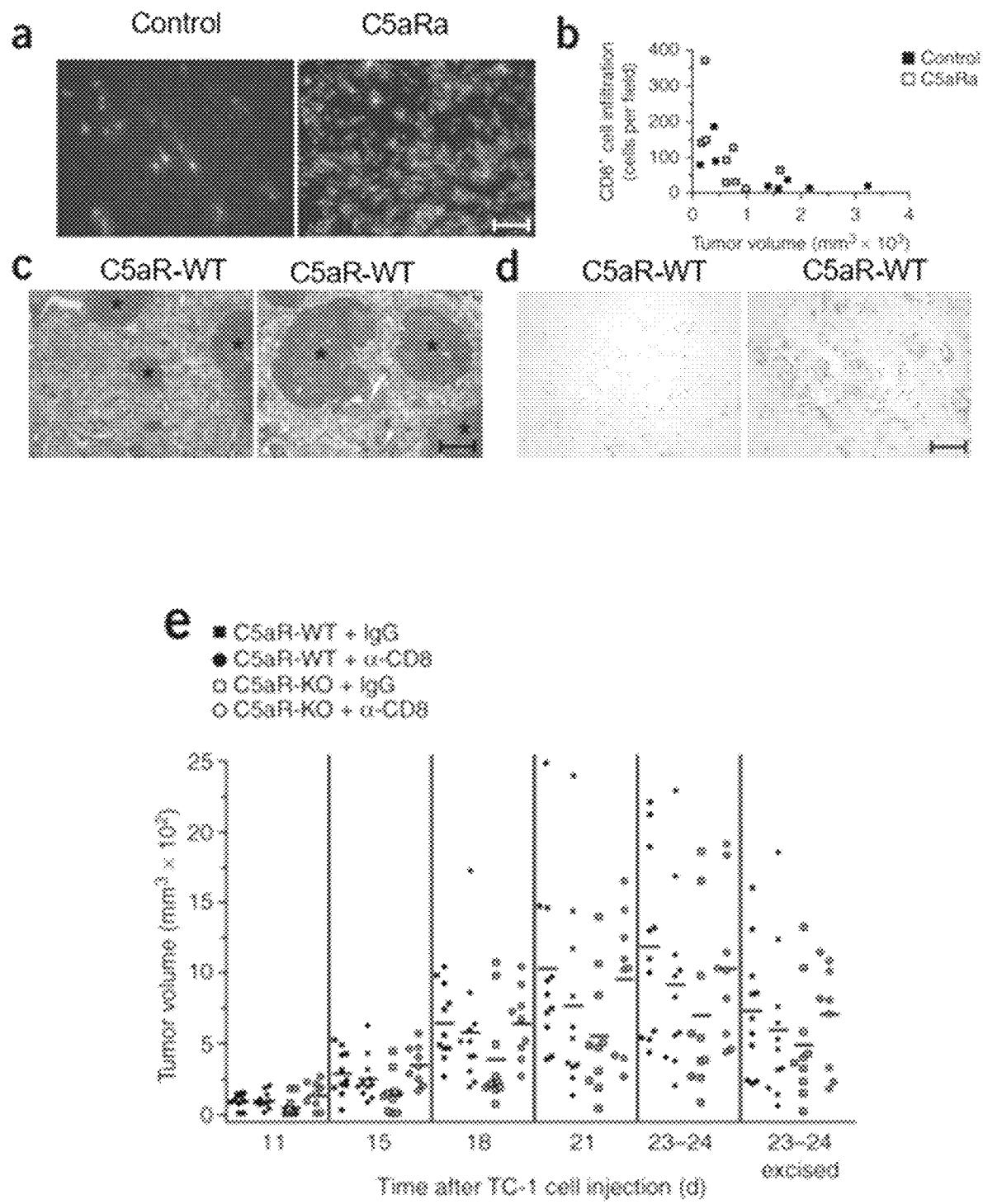
FIG. 4, comprising
Figure 5:
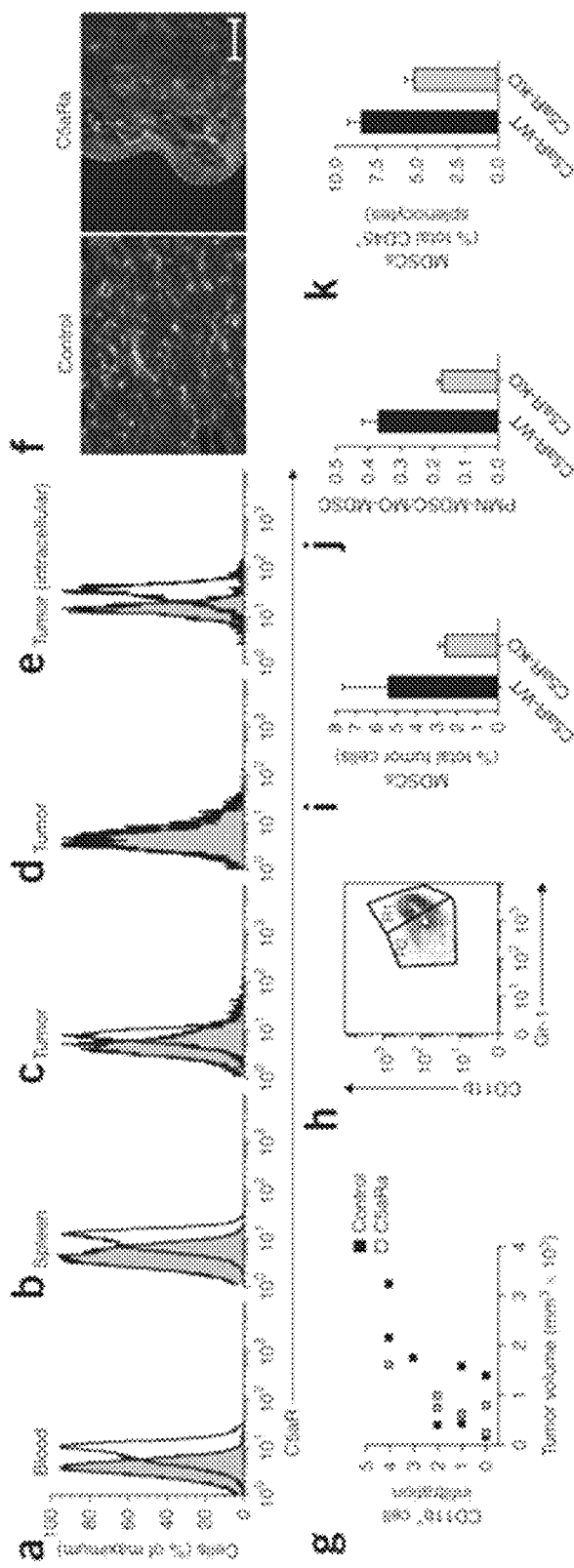
FIG. 5, comprising
Figure 6:
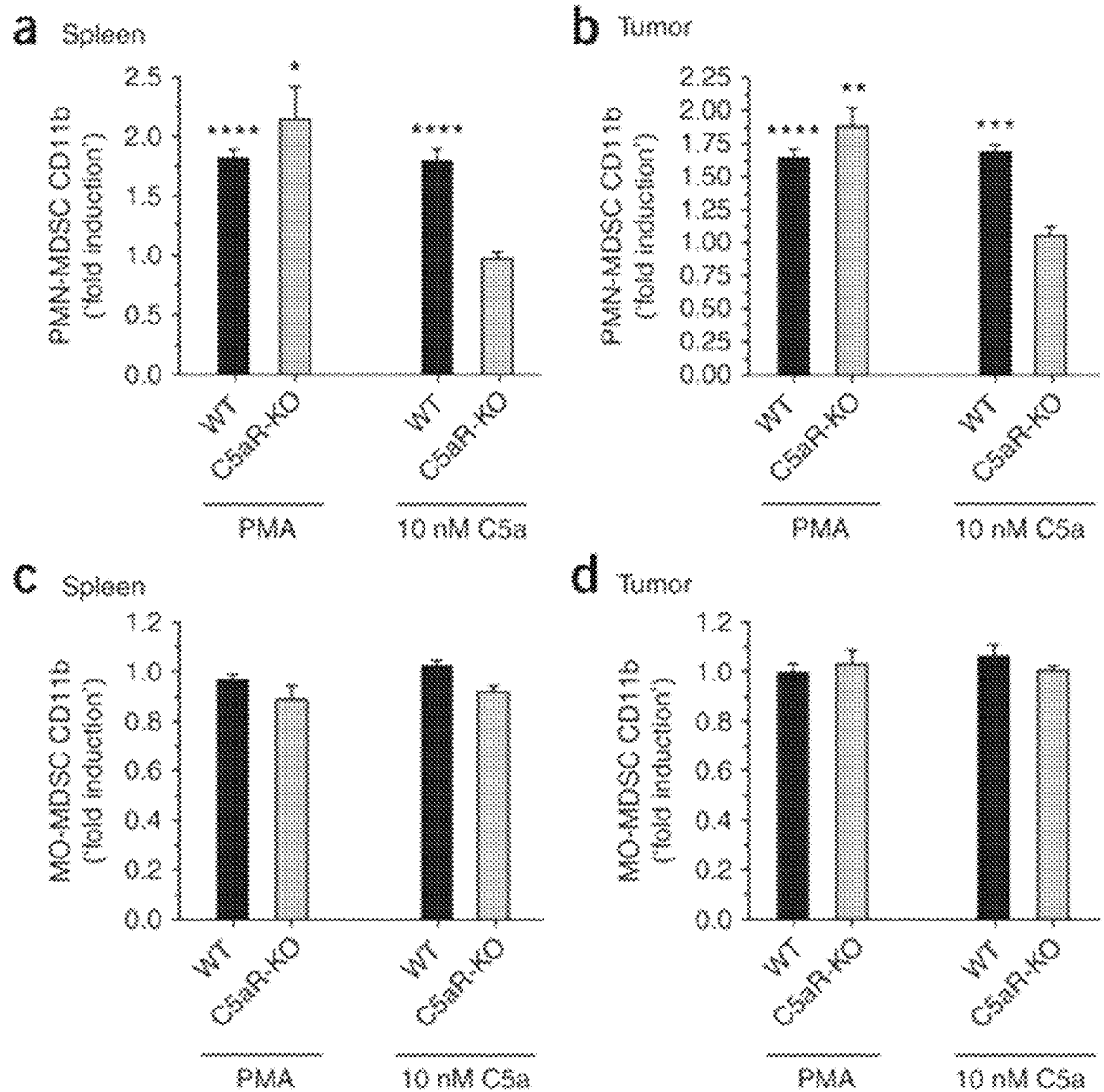
FIG. 6, comprising
Figure 7:
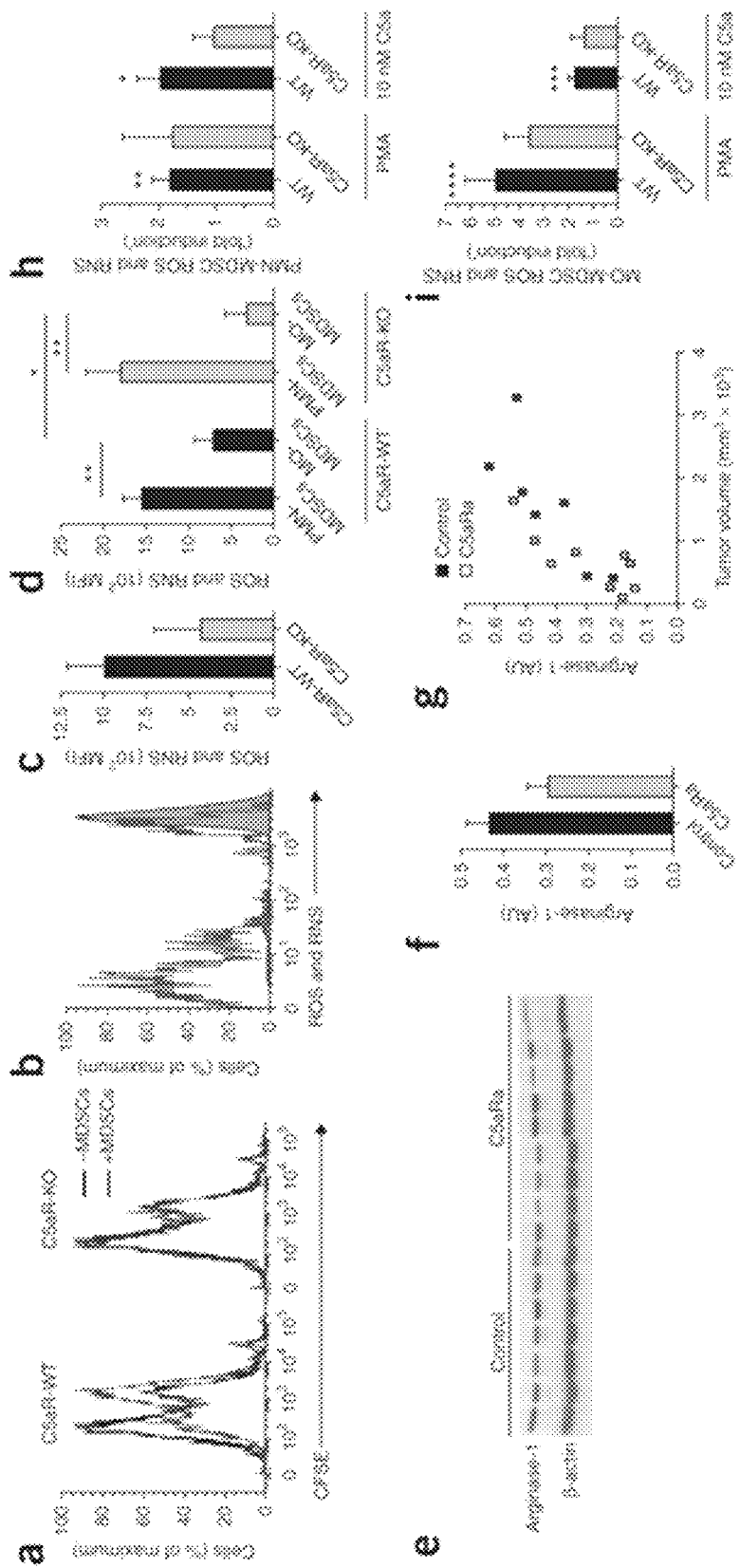
FIG. 7, comprising

The effect of genotype or treatment on tumor growth (FIGS. 1-4) was analyzed with two-way analysis of variance (ANOVA) using GraphPad Prism (GraphPad Software, Inc.); the Bonferroni post-test correction was applied to control for the occurrence of false-positives. To evaluate the significance of the correlation between tumor volumes and cell infiltrates (FIG. 4 and FIG. 5) or arginase concentrations (FIG. 7), the Pearson correlation test was applied (GraphPad Prism, GraphPad Software, Inc.). Unpaired two-tailed Student's t-test (Microsoft Excel; Microsoft Corp.) was used to test the significance of differences in the percentages of MDSCs in tumors and spleens (FIG. 5I-K), for assays of tumor cell proliferation and apoptosis and microvascular density, and for the number of T cells in $CD8^+$ T cell-depleted mice. To determine whether induction of CD11b (FIG. 6) or ROS (FIG. 7) over baseline values (set to equal 1) was significant, one sample t-test was used (GraphPad Prism, GraphPad Software, Inc.). Wilcoxon signed rank test (GraphPad Prism, GraphPad Software, Inc.) was applied to evaluate the significance of differences in median fluorescence values proportional to ROS/RNS production by MDSCs (FIG. 7). A p value equal to or less than 0.05 was considered significant.

Example 2

Studies were performed to determine whether complement effector proteins could promote tumor development. Many of the functions of complement are mediated by complement effectors such as C3a, C5a and MAC that are generated during the process of complement activation. It was hypothesized that these complement effectors are similarly generated during tumor development. In order to test this hypothesis, the TC-1 syngeneic model of cervical cancer in mice was used. In this model, flank tumors rapidly develop after subcutaneous (s.c.) injection of cancer cells. The activation of complement was monitored in these tumor-engrafted mice by immunofluorescent staining, which showed that C3 cleavage products were extensively deposited along the tumor vasculature in wild-type mice. As expected, staining was not observed in tumors from C3-deficient mice (data not shown), whereas in benign tissue surrounding tumors in wild-type mice only scattered C3 deposits were visible. C3 is the main protein of the complement activation cascade, at which most of the currently known pathways of complement activation converge (Sahu et al., 2001, Immunol. Rev. 180:35-48). Therefore, the cleavage of C3, as demonstrated by the presence of its cleavage products in tumor tissue, suggests that the activation of complement proteins had occurred in these tumor-bearing mice and had led to the generation of complement effectors. Given that, using available assays, no substantial increase in the concentrations of circulating C3 cleavage fragments in the plasma of these mice was seen (data not shown). These data point to a local and limited activation of complement in the tumor microenvironment rather than systemic complement activation, highlighting the specificity of this phenomenon for tumors.

Example 3

Because the formation of C3 convertase is the key point in the complement cascade, the elimination of C3 prevents the generation of complement effectors (Markiewski et al., 2007, Am. J. Pathol. 171:715-727) and eliminates a wide range of activities that are mediated by these molecules. As described in the previous example, deposition of C3 cleavage products was detected in the microenvironment of TC-1 tumors. This example describes an assessment of the levels of tumor growth in C3-deficient mice after subcutaneous (s.c.) inoculation with TC-1 tumor cells. This animal model is viewed as a model of cervical (uterine cervix) carcinoma. Tumor volumes measured at various times after s.c. inoculation of tumor cells were significantly reduced in the C3-deficient mice as compared with wild-type littermate controls at all the time points examined (FIG. 1). The absence of the deposition of C3 cleavage products in tumor tissue from C3-deficient mice demonstrated that the injected TC-1 cells were not producing C3 to reconstitute this deficiency. In addition, the concentrations of C3 in the sera of C3-deficient and control mice was monitored throughout the experiment. None of the C3-deficient mice showed detectable concentrations of C3 in their sera, nor was there an increase in the amount of C3 in the wild-type control mice, as determined by ELISA (data not shown). Thus, the impairment of tumor growth in mice lacking C3 strongly suggests that complement and complement activation are intimately involved in this process.

To elucidate the mechanisms of complement activation (classical, lectin and/or alternative pathways) in TC-1 tumors, tumor growth was assessed in mice deficient in complement protein C4 or complement factor B (fB), as well as their littermate controls, after s.c. inoculation with TC-1 tumor cells. C4 deficiency resulted in greatly reduced tumor growth (FIG. 2A). Given that C4 is required for the formation of the classical or lectin pathway C3 convertases, these results suggest the contribution of one of these pathways to complement activation and subsequent C3 cleavage in engrafted tumors. Deficiency of fB had no substantial effect on tumor growth (FIG. 2B), ruling out any major contribution of the alternative pathway, since fB is an essential component of the alternative pathway C3 convertase.

To dissect whether the classical or lectin pathway is involved in complement activation in tumor tissue, TC-1 tumors from wild-type mice were evaluated for the deposition of complement proteins which initiate these pathways. Immunofluorescent detection of C1q, using C1q antibody revealed moderate complement protein C1q deposits within tumor vasculature, whereas mannan binding lectin (MBL) deposition did not have clear association with tumor blood vessels since immunofluorescent staining for both C1q and MBL did not reveal colocalization. Since C1q initiates the classical pathway of complement activation and C1q deposition followed the pattern characteristic for C3 deposits, it was concluded that this pathway is the main contributor to complement activation in engrafted tumors. The functional relevance of the lectin pathway for complement activation in engrafted tumors remains to be established.

The C5a anaphylatoxin activates several cellular responses that are involved in tumor growth and progression, including the expression of adhesion molecules on endothelial cells and the release of various cytokines from leukocytes (Monk et al., 2007, Br. J. Pharmacol. 152:429-448). These properties of C5a and the results obtained from our study of C3-deficient mice prompted us to investigate whether C5a is required for tumor growth in our model. For this purpose, the C5a receptor (C5aR) was blocked in tumor-bearing wild-type mice with the hexapeptide AcF[OPdChaWR] (C5aR antagonist) (Finch et al., 1999, J. Med. Chem. 42:1965-1974), beginning treatment one week after tumor cell injection.

The pharmacological blockade of the C5aR with this antagonist resulted in impaired tumor growth in the antagonist-treated mice when compared to control mice treated with PBS (FIG. 3A). To estimate whether the therapeutic effectiveness of the C5aR antagonist in retarding tumor growth was comparable to the effects achieved by the treatment of tumor bearing mice with broadly used anti-cancer drugs, tumor volumes were also assessed in wild-type mice treated with the established anti-cancer drug paclitaxel (Taxol) alone, at a dose previously shown to suppress tumor growth (Holtz et al., 2008, J. Transl. Med. 6:2). A comparison between the tumor volumes in the mice treated with the C5aR antagonist and those treated with Taxol showed that inhibition of tumor growth by the complement inhibitor was comparable to that achieved by treatment with this anti-cancer therapeutic (FIG. 3A).

The specificity of our findings was validated by assessing tumor growth in mice deficient in the C5aR. Consistent with the hypothesis and the results seen in the C5aR antagonist-treated mice, these C5aR-deficient mice exhibited significantly decreased tumor volumes when compared to their littermate controls (FIG. 3B). Further, it was found that the suppressive effect of genetic C5aR deficiency on tumor growth was similar to that obtained by treating wild-type mice with Taxol, indicating that lack of the C5aR inhibits tumor growth as well as an established anti-cancer drug (FIG. 3C). These experiments also suggested that C5aR expressed on host cells is involved in the regulation of tumor growth. It was initially observed that C5aR mRNA was not present in TC-1 cells under culture conditions (FIG. 3D), but the possibility could not be excluded that C5aR is upregulated in tumor cells in vivo. However, if C5aR signaling on TC-1 cells contributed to tumor growth, these cells should still grow in C5aR-deficient mice, as only the host cells lack the ability to express C5aR in these mice. Therefore, these experiments suggest that C5a contributes to the control of tumor growth by acting primarily on receptors expressed by host cells, irrespective of their expression on tumor cells.

To exclude the possibility that that the effect of the C5aR antagonist on tumor growth was related to non-specific cytotoxicity of this peptide toward tumor cells, it was evaluated whether the treatment of C5aR-deficient mice with C5aR antagonist further delayed tumor growth. In addition, we also used the peptide-AcF[OPdChaA(d)R] (control peptide), which has the same length and similar physicochemical properties as C5aR antagonist but does not have the ability to block C5aR signaling (Finch et al., 1999, J. Med. Chem. 42:1965-1974; Johswich et al., 2006, J. Biol. Chem. 281:39088-39095). Use of this control peptide was meant to verify whether alteration of the cellular microenvironment by injected peptides, rather than their biological activity, influences the rate of tumor growth.

The treatment of C5aR-deficient mice did not induce any further inhibition of tumor growth in comparison to mice treated with control peptide. In addition, TC-1 tumors grew slower in C5aR-deficient mice in comparison to wild-type controls, as observed in previous experiments, regardless of the treatment of both cohorts with the control peptide. Therefore, it was concluded that the effects of the C5aR antagonist on tumor growth in wild-type mice are exclusively related to the property of this peptide to disable C5aR function.

Example 4

To elucidate the mechanism by which C5a contributes to tumor growth, several parameters were assessed that influence tumor development (tumor cell proliferation and apoptosis, and the extent of angiogenesis) in end-point tumor specimens harvested from mice treated with either C5aR antagonist or PBS. There were only minimal differences between experimental groups in these parameters without statistical significance. This result suggests that other mechanisms, such as tumor cell elimination by the immune system, may contribute to the phenotype observed in mice in which C5a activity was blocked. Given the crucial role of cytotoxic T cells in controlling tumor growth, the absolute number of $CD8^+$ cells infiltrating the tumor tissue in C5aR antagonist-treated and control mice was compared.

Immunofluorescent staining revealed that mice in which C5aR signaling was blocked had tumors heavily infiltrated by $CD8^+$ cells, whereas in a majority of the control mice only a few of these T cells were present in whole-tumor sections (FIG. 4A). Furthermore, quantification of the $CD8^+$ infiltrates showed that there was also an inverse correlation between tumor size and the number of infiltrating $CD8^+$ cells (FIG. 4B).

These data were corroborated by our observation that the percentages of activated $CD3^+CD8^+(CD4^-)CD25^+$ and $CD3^+CD8^+(CD4^-)CD69^+$ T cells were slightly higher in tumors from C5aR-deficient mice than in those from their littermates (n=3), as estimated by flow cytometry (28.7±3.4% vs. 21.1±1.8% for $CD25^+$ and 24.4±3.2% vs. 16.7±2.2% for $CD69^+$, respectively). However, these differences did not reach statistical significance. Finally, it was observed that the size of the white pulp follicles in the spleen was increased, and the proliferation of lymphoid cells residing in these structures was higher in C5aR-deficient mice bearing tumors than in their tumor-bearing littermate controls (FIG. 4C and FIG. 4D).

These results suggested that C5a modulates the CD8$^+$ T cell mediated anti-tumor immune response. Therefore, it was hypothesized that slower tumor growth in C5aR-deficient mice and in wild-type mice treated with C5aR antagonist is a result of the infiltration of these tumors by CD8$^+$ T cells. To verify this hypothesis experiments were conducted in which CD8$^+$ T cells were depleted by treatment with CD8-specific antibody in C5aR-deficient and control mice inoculated with tumors cells, expecting that this depletion of CD8$^+$ T cells in C5aR-deficient mice should result in an increased rate of tumor growth. Indeed, even the partial elimination of these cells from C5aR-deficient mice resulted in accelerated tumor growth in these mice to the rate observed in wild-type controls (FIG. 4E). CD8$^+$ T cell depletion did not affect tumor growth in wild-type controls. This result was also expected, based on the observation that only a few CD8$^+$ T cells infiltrated tumors in untreated wild-type mice (FIG. 4A). Preliminary experiments in mice not bearing tumors showed that injections of CD8 antibody at a dose selected to deplete CD8$^+$ T cells resulted in more than 95% depletion of CD8$^+$ T cells (data not shown). However, the monitoring of peripheral blood and spleen of mice bearing tumors revealed that by injecting CD8 antibody we achieved only partial depletion of CD8$^+$ T cells in these mice, Importantly, though, the degree of CD8$^+$ T cell depletion strongly and positively correlated with the rate of tumor growth in C5aR-deficient mice. This positive correlation confirms that the acceleration of tumor growth in C5aR-deficient mice that had been injected with CD8 antibody was a result of CD8$^+$ T cell depletion. Furthermore, tumors from C5aR-deficient mice treated with CD8 antibody had a lower number of CD8$^+$ T cells than tumors from C5aR-deficient mice treated with control rat IgG, as demonstrated by immunofluorescence analysis.

Example 5

The observations detailed herein suggested that C5a signaling contributes to the inhibition of the immune response against tumor cells. Cells of myeloid origin, including MDSCs and tumor-associated macrophages (TAMs), have been shown to be important for suppression of the immune response against tumor antigens and promotion of tumor growth in mice and humans. In addition, it is known that granulocytes, monocytes, and tissue macrophages, which are the mature counterparts of MDSCs, express abundant C5aR (Guo et al., 2005, Ann. Rev. Immunol. 23:821-852). Moreover, it has been demonstrated herein that complement proteins were deposited in tumor tissue (FIG. 1), suggesting the occurrence of local complement activation, with the concomitant generation of C5a. Therefore, it was hypothesized that C5a might contribute to the inhibitory properties of MDSCs.

Our initial studies showed that CD45$^+$CD11b$^+$Gr-1$^+$ MDSCs, isolated from the spleen and blood of naive mice, expressed C5aR to a similar extent as that observed in mature granulocytes and monocytes. Similarly, we observed C5aR expression on the surface of MDSCs circulating in the peripheral blood (FIG. 5A) or residing in the spleen (FIG. 5B) of tumor-bearing mice. The expression of C5aR was reduced on the surface of tumor-associated MDSCs (FIG. 5C) in comparison to peripheral blood and spleen MDSCs. Surprisingly, MDSCs isolated from the tumors of some wild-type mice did not show any surface expression of C5aR (FIG. 5D). However, when MDSCs from the same tumors were permeabilized before staining, C5aR was clearly detectable in the cytoplasm (FIG. 5E). This result demonstrated that C5aR was internalized in tumor associated MDSCs. The rapid internalization of a majority of G-coupled receptors occurs as a regulatory mechanism in response to the constant presence of ligands.

Since C5a is known as a strong chemoattractant (Guo et al., 2005, Ann. Rev. Immunol. 23:821-852), it was investigated the involvement of C5a in the migration of myeloid-origin cells into tumors. Immunofluorescent staining of tumor sections showed that the number of cells expressing CD11b was lower in C5aR antagonist-treated mice than in mice treated with PBS (FIG. 5F). Interestingly, CD11b$^+$ cells in C5aR antagonist-treated mice were located only at the periphery of the tumors, whereas in control mice they were found throughout the tumor sections. A positive correlation was seen between the number of CD11b$^+$ cells and the tumor volume in both experimental groups (FIG. 5G).

Flow cytometry analysis of CD45$^+$CD11b$^+$Gr-1$^+$ cells isolated from tumors from C5aR-deficient and control mice revealed the presence of two distinct subpopulations of MDSCs differing by the extent of expression of CD11b and Gr-1 (FIG. 5H). These subpopulations corresponded to mononuclear (MO)- and polymorphonuclear (PMN)-MDSCs. PMN-MDSCs were characterized by higher expression of both CD11b and Gr-1 (R1 in FIG. 5H) in comparison to MO-MDSCs (R2 in FIG. 5H). Although the percentage of total MDSCs isolated from tumors from wild-type mice was higher than the percentage of these cells in tumors from C5aR-deficient mice, this difference did not reach statistical significance (FIG. 5I). However, it was observed that the ratio of PMN-MDSCs to MO-MDSCs was significantly higher in tumors from wild-type mice in comparison to tumors from C5aR-deficient mice (FIG. 5J). Therefore, it was concluded that C5a influences mainly the migration of PMN-MDSCs into tumors. In addition, the percentage of CD11b$^+$Gr-1$^+$ MDSCs in the CD45$^+$ cell population isolated from the spleens of wild-type mice was higher than the percentage of these cells existing in the spleens of C5aR-deficent mice (FIG. 5K). This observation suggests the involvement of C5a in the processes of MDSC migration and accumulation into peripheral lymphoid organs.

The migration of PMN-MDSCs to tumors requires crossing of the endothelial barrier by MDSCs. Leukocytes, in order to leave the circulation and migrate to interstitial tissues, require the interaction of their integrins with adhesion molecules on endothelial cells. It was hypothesized that the same mechanisms apply to MDSCs migrating to tumor tissue. Since CD11b is the $\alpha_m$ subunit of integrin CR3, which interacts with ICAM-1 expressed on endothelial cells during leukocyte extravasation, the changes in CD11b expression were evaluated in MDSCs obtained from tumors and spleens after C5a stimulation in vitro. Wild-type PMN-MDSCs isolated from spleens and tumors showed significant increase in the expression of CD11b after C5a stimulation (FIG. 6A and FIG. 6B), whereas MO-MDSCs did not respond to C5a stimulation by upregulating CD11b (FIG. 6C and FIG. 6D). These results strongly support the hypothesis that C5a contributes to the recruitment of PMN-MDSCs to tumors. The specificity of these findings was confirmed by the lack of CD11b upregulation in C5aR-deficient MDSCs stimulated with C5a (FIG. 6A through FIG. 6D), despite the response of these cells to phorbol myristate acetate (PMA) (FIG. 6A, FIG. 6B, and FIG. 6D), which was used as a positive control to determine the capability of MDSCs to respond to in vitro stimuli.

Example 6

The capacity of Gr-1+ MDSCs isolated from tumors obtained from C5aR-deficient and sufficient mice to inhibit the proliferation of CD3+ T cells originating from the spleens of naive mice was analyzed. MDSCs recovered from the tumor microenvironment of C5aR-deficient mice showed either a total inability or a weaker capacity to inhibit phytohemagglutinin (PHA)-induced T cell proliferation than did MDSCs from tumors of littermate controls (FIG. 7A). These observations suggest that C5a contributes not only to the migration of MDSCs into tumors but also to their functional capacity to inhibit the T cell response against tumor cells.

Given that MDSCs are known to inhibit the anti-tumor antigen-specific CD8+ T cell response by producing large amounts of highly suppressive ROS and RNS (Kusmartsev et al., 2004, J. Immunol. 172:989-999), and that C5a is involved in the regulation of ROS and RNS synthesis in macrophages (Daniel et al., 2006, J. Immunol. 177:4688-4698) and neutrophils (Guo et al., 2003, FASEB J. 17:1889-1891), which are thought to be mature counterparts of MDSCs, it was hypothesized that C5a influences the suppressive ability of MDSCs through the regulation of their ROS and RNS production. As demonstrated by flow cytometry analysis, the overall amount of ROS and RNS in MDSCs isolated from tumors from C5aR-deficient mice was strikingly lower in comparison to the amounts detected in MDSCs from tumors from wild-type controls (FIG. 7B and FIG. 7C). Since it had been observed that C5a influenced the ratio of MO-MDSCs to PMN-MDSCs (FIG. 5J), the contribution of both subpopulations to ROS and RNS production was analyzed. It was observed that in both C5aR-deficient and sufficient mice, tumor-associated PMN-MDSCs produced significantly higher amounts of ROS and RNS than corresponding MO-MDSCs (FIG. 7D). However, when comparing the specific subpopulation of PMN-MDSCs between C5aR-deficient and sufficient mice, a difference in ROS or RNS production was not seen (FIG. 7D). Conversely, MO-MDSCs from tumors growing in C5aR-deficient mice synthesized less ROS and RNS than their wild-type counterparts (FIG. 7D). Therefore, it appears that C5a augments ROS and RNS production only in MO-MDSCs. However, considering that C5a increases the migration of ROS- and RNS-rich PMN-MDSCs into the tumor, high amounts of ROS and RNS in the tumor microenvironment of wild-type mice is a net effect of dual C5a activity. C5a induces the migration of highly suppressive, ROS- and RNS-rich PMN-MDSCs into the tumor microenvironment; additionally, it increases the production of ROS and RNS by MO-MDSCs.

Arginase-1 activity is essential for the immunosuppressive capabilities of MDSCs and contributes to the production of ROS and RNS by these cells (Marx et al., 2008, Science 319:154-156). Therefore, the expression of this enzyme was analyzed in available whole-cell extracts from tumors harvested from mice treated with C5aR antagonist or control mice (FIG. 7E). Arginase-1 expression was only slightly lower in mice treated with C5aR antagonist without reaching statistical difference (FIG. 7F). However, a strong significant positive correlation was observed between arginase-1 expression and tumor volume (FIG. 7G) in both groups with the correlation coefficient (Pearson r) equal to 0.802.

To further verify the results obtained from these in vivo studies, MDSCs from spleens and tumors of wild-type mice were stimulated to produce ROS and RNS by incubating them with various concentrations of C5a in vitro. MDSCs isolated from C5aR-deficient mice were used as an additional control for these experiments. Both subpopulations of MDSCs isolated from spleens responded to C5a stimulation by increasing their ROS and RNS production in comparison to non-stimulated cells obtained from the same mouse (FIG. 7H and FIG. 7I). As expected, MDSCs from spleens of C5aR-deficient mice did not respond to C5a stimulation, despite the brisk response to PMA stimulation (FIG. 7H and FIG. 7I). Tumor-associated MDSCs did not respond to C5a stimulation, regardless of which subpopulation of MDSCs was analyzed (data not shown). It was concluded that the unresponsiveness of tumor-associated MDSCs to in vitro C5a stimulation was a result of the strong stimulation of these cells for ROS and RNS production in vivo in the tumor microenvironment and the exhaustion of this system; therefore, further stimulation of these cells in vitro failed. This conclusion was supported by the substantially higher initial ROS and RNS production in tumor-associated MDSCs in comparison to MDSCs obtained from spleens (data not shown) and the lack of an increase in ROS or RNS production in tumor-associated MDSCs in response to PMA stimulation (data not shown).

The present invention is not limited to the embodiments described and exemplified above, but is capable of variation and modification within the scope of the appended claims.

What is claimed:

1. A method for treating an individual having a tumor, the method comprising the steps of:
   (1) providing an individual having a tumor;
   (2) administering to the individual a therapeutically effective amount of a complement inhibitor comprising a pharmaceutically acceptable carrier and at least one polypeptide having an amino acid sequence selected from the group consisting of SEQ ID NO:2 and SEQ ID NO:3; and
   (3) measuring the size of the tumor in the individual;
   wherein the administering of the complement inhibitor results in a reduction in tumor size, or a delay or prevention of increase in tumor size, thereby treating the individual having the tumor.

2. The method of claim 1 wherein the individual is human.

3. The method of claim 1, wherein the complement inhibitor is administered at or targeted to the site of the tumor.

4. The method of claim 1, wherein the complement inhibitor is administered systemically.

5. The method of claim 1, wherein the complement inhibitor is administered together or concurrently with, or sequentially before or after, at least one other anti-cancer treatment.

6. The method of claim 1, wherein tumor size is measured by one or more of length, width, depth, volume and weight of the tumor.

7. A method of reducing or delaying growth or development of a tumor disposed within an individual, comprising the steps of:
   (1) providing the individual in which a tumor is disposed;
   (2) administering to the individual a therapeutically effective amount of a complement inhibitor comprising a pharmaceutically acceptable carrier and at least one polypeptide having an amino acid sequence selected from the group consisting of SEQ ID NO:2 and SEQ ID NO:3; and
   (3) measuring the size of the tumor;
   wherein a reduction in tumor size, or a delay or prevention of increase in tumor size, is indicative of reducing or delaying the growth or development of the tumor disposed within the individual.

8. The method of claim 7, wherein the individual is human.

9. The method of claim 7, wherein the complement inhibitor is administered at or targeted to the site of the tumor.

10. The method of claim 7, wherein the complement inhibitor is administered systemically.

11. The method of claim 7, wherein the complement inhibitor is administered together or concurrently with, or sequentially before or after, at least one other anti-cancer treatment.

12. The method of claim 7, wherein tumor size is measured by one or more of length, width, depth, volume and weight of the tumor.

* * * * *

UNITED STATES PATENT AND TRADEMARK OFFICE
CERTIFICATE OF CORRECTION

PATENT NO. : 10,632,170 B2
APPLICATION NO. : 12/918101
DATED : April 28, 2020
INVENTOR(S) : Lambris et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1024 days.

Signed and Sealed this
First Day of December, 2020

Andrei Iancu
*Director of the United States Patent and Trademark Office*